(12) United States Patent
Ish-Am Radian et al.

(10) Patent No.: US 11,970,416 B2
(45) Date of Patent: Apr. 30, 2024

(54) BIO-CLAYS COMPOSITES FOR ALDEHYDE REMEDIATION

(71) Applicant: TECHNION RESEARCH & DEVELOPMENT FOUNDATION LIMITED, Haifa (IL)

(72) Inventors: Adi Ish-Am Radian, Kiryat Tivon (IL); Ayelet Fishman, Haifa (IL); Yael Zvulunov, Bnei Dror (IL); Zohar Ben-Barak Zelas, Moshav Nahalal (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 600 days.

(21) Appl. No.: 17/058,265

(22) PCT Filed: May 23, 2019

(86) PCT No.: PCT/IL2019/050589
§ 371 (c)(1),
(2) Date: Nov. 24, 2020

(87) PCT Pub. No.: WO2019/224829
PCT Pub. Date: Nov. 28, 2019

(65) Prior Publication Data
US 2021/0114907 A1 Apr. 22, 2021

Related U.S. Application Data

(60) Provisional application No. 62/675,950, filed on May 24, 2018.

(51) Int. Cl.
C02F 3/34 (2023.01)
C02F 3/10 (2023.01)
(Continued)

(52) U.S. Cl.
CPC .......... *C02F 3/34* (2013.01); *C02F 3/107* (2013.01); *C12N 11/089* (2020.01); *C12N 11/091* (2020.01); *C02F 2101/34* (2013.01)

(58) Field of Classification Search
None
See application file for complete search history.

(56) References Cited

U.S. PATENT DOCUMENTS 3,594,212 A 7/1971 Ditsch
4,824,577 A * 4/1989 Schwitzgelbel ....... C08G 14/10
210/668

(Continued)

FOREIGN PATENT DOCUMENTS

CN 105800863 A 7/2016
WO WO 91/19675 * 12/1991
WO WO-03106585 A1 * 12/2003 ............... C09K 8/12

OTHER PUBLICATIONS

R. Ganigar, G. Rytwo, Y. Gonen, A. Radian & Y.G. Mishael, Polymer-clay nanocomposites for the removal of trichlorophenol and trinitrophenol from water, Appl. Clay Sci. 49 (2010) 311-316. doi:10.1016/j.clay.2010.06.015.

(Continued)

Primary Examiner — Chester T Barry
(74) Attorney, Agent, or Firm — The Roy Gross Law Firm, LLC; Roy Gross

(57) ABSTRACT

The present invention is directed to clay composites comprising at least one polycation attached to the clay surface and at least one aldehyde degrading microorganism and uses thereof for removal of aldehyde from aldehyde containing environments.

19 Claims, 23 Drawing Sheets

Specification includes a Sequence Listing.

(51) Int. Cl.
*C12N 11/089* (2020.01)
*C12N 11/091* (2020.01)
*C02F 101/34* (2006.01)

(56) References Cited

U.S. PATENT DOCUMENTS 5,580,770 A 12/1996 DeFilippi
6,395,522 B1* 5/2002 DeFilippi ............... C02F 3/108
435/177

OTHER PUBLICATIONS

A. Radian & Y. Mishael. Effect of humic acid on pyrene removal from water by polycation-clay mineral composites and activated carbon, Environ. Sci. Technol. 46 (2012) 6228-6235. doi:10.1021/es300964d.

A. Radian, M. Fichman & Y. Mishael. Modeling binding of organic pollutants to a clay-polycation adsorbent using quantitative structural-activity relationships (QSARs), Appl. Clay Sci. 116-117 (2015) 241-247. doi:10.1016/j.clay.2015.03.021.

Zadaka D, Nir S, Radian A. & Mishael YG. Atrazine removal from water by polycation-clay composites: effect of dissolved organic matter and comparison to activated carbon. Water Res. Feb. 2009;43(3):677-83. doi: 10.1016/j.watres.2008.10.050. Epub Nov. 8, 2008. PMID: 19038414.

B. Sarkar, Y. Xi, M. Megharaj, G.S.R. Krishnamurti, M. Bowman, H. Rose & R. Naidu, Bioreactive organoclay: A new technology for environmental remediation, Crit. Rev. Environ. Sci. Technol. 42 (2012) 435-488. doi:10.1080/10643389.2010.518524.

A. Radian, D. Michaeli, C. Serban, R. Nechushtai & Y.G. Mishael. Bioactive apo-ferredoxin-polycation-clay composites for iron binding, J. Mater. Chem. 20 (2010) 4361-4365. doi:10.1039/c0jm00232a.

B. Ruan, P. Wu, X. Lai, H. Wang, L. Li, L. Chen, C. Kang, N. Zhu, Z. Dang & G. Lu. Effects of *Sphingomonas* sp. GY2B on the structure and physicochemical properties of stearic acid-modified montmorillonite in the biodegradation of phenanthrene, Appl. Clay Sci. 156 (2018) 36-44. doi:10.1016/j.clay.2018.01.009.

A. Mandal, B. Biswas, B. Sarkar, A.K. Patra & R. Naidu. Surface tailored organobentonite enhances bacterial proliferation and phenanthrene biodegradation under cadmium co-contamination, Sci. Total Environ. 550 (2016) 611-618. doi:10.1016/j.scitotenv.2016.01.164.

B. Ruan, P. Wu, M. Chen, X. Lai, L. Chen, L. Yu, B. Gong, C. Kang, Z. Dang, Z. Shi & Z. Liu, Immobilization of *Sphingomonas* sp. GY2B in polyvinyl alcohol-alginate-kaolin beads for efficient degradation of phenol against unfavorable environmental factors, Ecotoxicol. Environ. Saf. 162 (2018) 103-111. doi: 10.1016/J.ECOENV.2018.06.058.

N. Öztekin, A. Alemdar, N. Güngör & F.B. Erim, Adsorption of polyethyleneimine from aqueous solutions on bentonite clays, Mater. Lett. 55 (2002) 73-76. doi:10.1016/S0167-577X(01)00622-X.

C.-C. Chen & P.-L. Kuo, Gold nanoparticles prepared using polyethylenimine adsorbed onto montmorillonite, J. Colloid Interface Sci. 293 (2006) 101-107. doi:10.1016/J.JCIS.2005.06.051.

Y.-F. Chu, C.-H. Hsu, P.K. Soma & Y.M. Lo. Immobilization of bioluminescent *Escherichia coli* cells using natural and artificial fibers treated with polyethyleneimine, Bioresour. Technol. 100 (2009) 3167-3174. doi:10.1016/j.biortech.2009.01.072.

Afkhami, A., Bagheri, H., & Madrakian, T. Alumina nanoparticles grafted with functional groups as a new adsorbent in efficient removal of formaldehyde from water samples. Desalination, 281 (2011) 151-158. doi:10.1016/j.desal.2011.07.052.

J. E. Fernandez and G. B. Butler. The Reaction of Secondary Amines with Formaldehyde. The Journal of Organic Chemistry 1963 28 (11), 3258-3259 DOI: 10.1021/jo01046a536.

Kallen, R.G. & Jencks, W.P. Equilibria for the reaction of amines with formaldehyde and protons in aqueous solution. A re-examination of the formol titration. J Biol Chem. Dec. 25, 1966;241(24):5864-78. PMID: 5954364.

Ewlad-Ahmed, A.M., Morris, M.A., Patwardhan, S.V. & Gibson, L.T. Removal of formaldehyde from air using functionalized silica supports. Environ Sci Technol. Dec. 18, 2012;46(24): 13354-60. doi: 10.1021/es303886q. Epub Dec. 6, 2012. PMID: 23181357.

S. Nuasaen, P. Opaprakasit & P. Tangboriboonrat. Hollow latex particles functionalized with chitosan for the removal of formaldehyde from indoor air, Carbohydr. Polym. 101 (2014) 179-187. doi:10.1016/j.carbpol.2013.09.059.

Kim, Y.H., Park, J.H., Lee, M., Kim, Y.H., Park, T.G. & Kim, S.W. Polyethylenimine with acid-labile linkages as a biodegradable gene carrier. J Control Release. Mar. 2, 2005;103(1):209-19. doi: 10.1016/j.jconrel.2004.11.008. Epub Dec. 15, 2004. PMID: 15710512.

Kazemi, S.H., Alizadeh, A., Mohamadi, R., Khodaei, M.M. & Kordestani, D. pH-regulated release of dopamine from well-ordered self-assembled monolayers: electrochemical studies. Mater Sci Eng C Mater Biol Appl. Dec. 1, 2013;33(8):5095-9. doi: 10.1016/j.msec.2013.07.007. Epub Jul. 13, 2013. PMID: 24094230.

Yan, J., Su, T., Cheng, F., Cao, J., Zhang, H. & He, B. Multifunctional nanoparticles self-assembled from polyethylenimine-based graft polymers as efficient anticancer drug delivery. Colloids Surf B Biointerfaces. Jul. 1, 2017;155:118-127. doi: 10.1016/j.colsurfb.2017.02.030. Epub Feb. 24, 2017. PMID: 28415029.

Sprung, A. A Summary of the Reactions of Aldehydes with Amines. Chemical Reviews 1940 26 (3), 297-338 DOI: 10.1021/cr60085a001.

Zvulunov, Y., Zelas, Z., Fishman, A., & Radian, A. (Jul. 2017) Clay-Polymer Composites for Chemical and Biological Remediation of Formaldehyde [Conference session]. International Clay Conference.

PCT International Search Report for International Application No. PCT/IL2019/050589, dated Aug. 25, 2019, 4pp.

PCT Written Opinion for International Application No. PCT/IL2019/050589, dated Aug. 25, 2019, 6pp.

PCT International Preliminary Report on Patentability for International Application No. PCT/IL2019/050589, dated Nov. 24, 2020, 7pp.

* cited by examiner

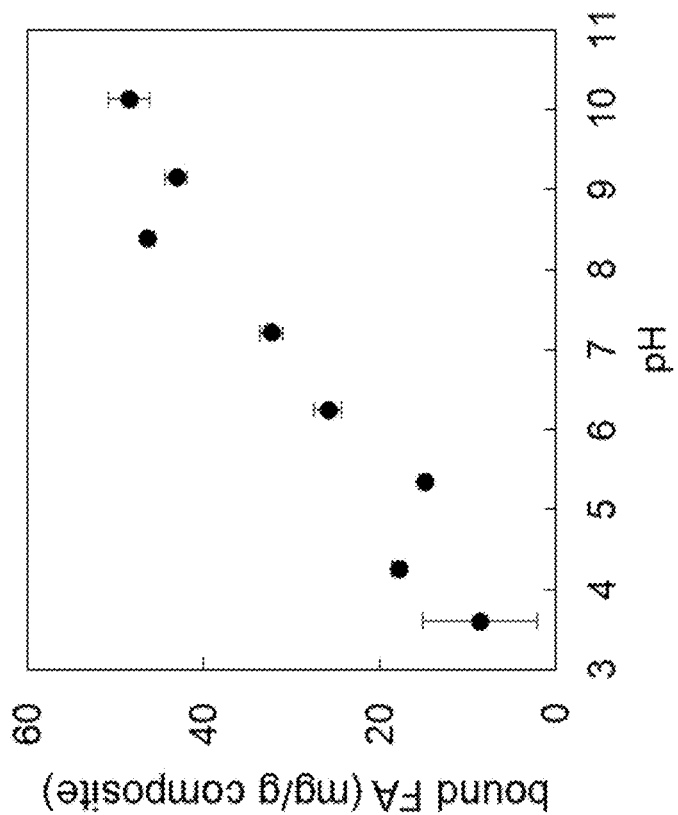
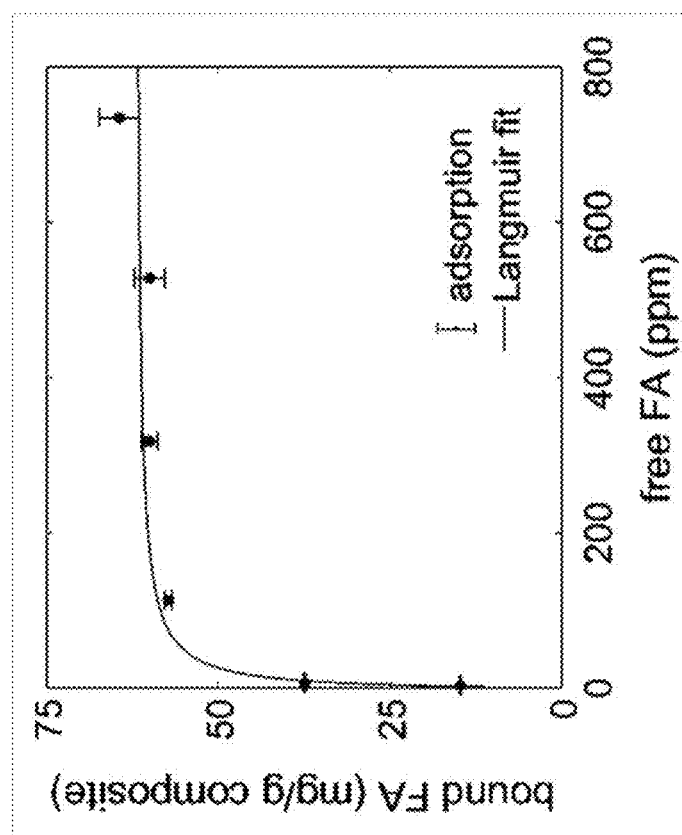
Figure 3B
Figure 3A

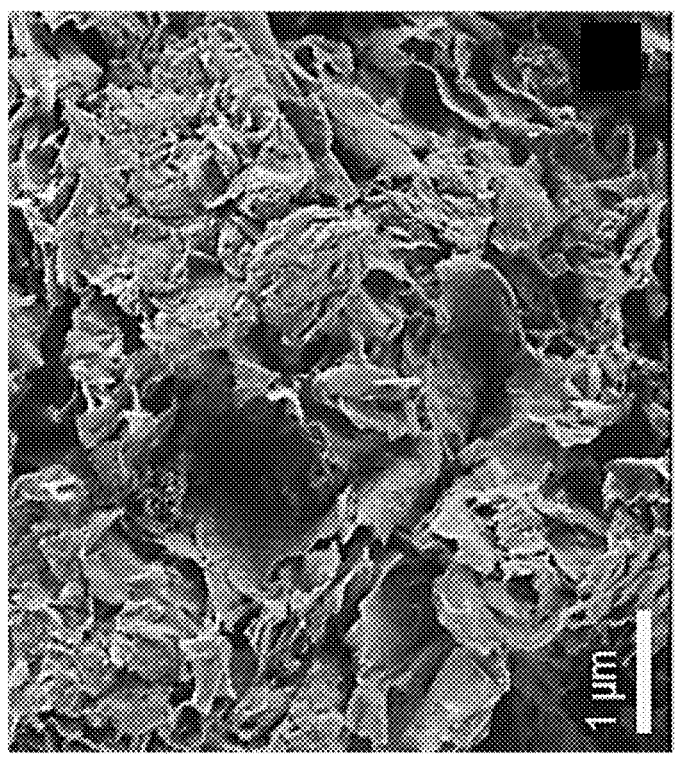
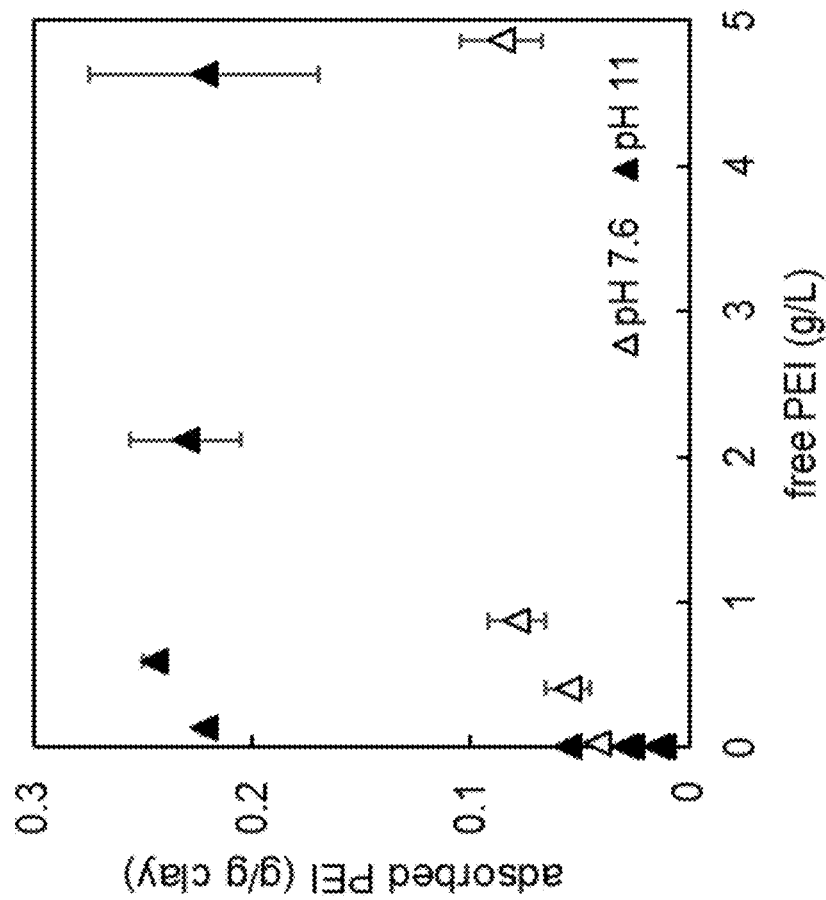
Figure 7A
Figure 7B

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: Synthetic

<400> SEQUENCE: 1
gagagtttga tcctggctca g          21

```
<210> SEQ ID NO 2
<211> LENGTH: 20
<212> TYPE: DNA
<213> ORGANISM: Artificial
<220> FEATURE:
<223> OTHER INFORMATION: Synthetic

<400> SEQUENCE: 2
ctacggctac cttgttacga                                              20
```

BIO-CLAYS COMPOSITES FOR ALDEHYDE REMEDIATION

CROSS REFERENCE TO RELATED APPLICATIONS

This application is a National Phase of PCT Patent Application No. PCT/IL2019/050589 having International filing date of May 23, 2019, which claims the benefit of priority to U.S. Provisional Patent Application No. 62/675,950 filed May 24, 2018 entitled "BIO-CLAYS COMPOSITES FOR FORMALDEHYDE REMEDIATION", the contents of which are incorporated herein by reference in their entirety.

FIELD OF THE INVENTION

The present invention, in some embodiments thereof, relates, inter alia, to compounds and clay composites comprising same, and uses thereof for removal and degradation of aldehyde.

BACKGROUND OF THE INVENTION

Aqueous wastes contain aldehydes, and in order to dispose aqueous wastes without danger to the environment, there is a need to neutralize the aldehydes.

Many industrial activities utilize formaldehyde (FA) as a key chemical in organic synthesis including: synthesis of special chemicals such as pentaerythritol and ethylene glycol, synthetic resins, paper products, medicinal products, drugs and other. Therefore, effluents arising from these applications may contain significant amounts of formaldehyde. These industrial processes produce large volumes of acidic and highly concentrated wastewater (3000-50,000 ppm FA, pH 3-4.5). Due to the toxic and carcinogenic nature of FA, such wastewaters need to be properly treated prior to release from the industrial plants.

Despite the growing need for efficient methods to treat aldehyde-rich and FA-rich wastewater, common technologies at the moment fall short.

SUMMARY OF THE INVENTION

According to one aspect, there is provided a composition comprising a mineral clay, at least one polycation attached to at least a portion of a surface of the mineral clay and at least one aldehyde degrading microorganism.

In some embodiments, the aldehyde comprises formaldehyde, acetaldehyde, propanal, glyoxal, methylglyoxal, nonanal, decanal, benzaldehyde, furan aldehydes, acrolein, anisaldehyde, and any combination thereof.

In some embodiments, a polycation is attached to at least 25% of the total mineral clay surface.

In some embodiments, a polycation has primary amine groups, secondary amine groups or a combination thereof.

In some embodiments, an aldehyde degrading microorganism is selected from *Methylobacterium, Paecilomyces, Pseudomonas, Aspergillus, Ralstonia*, methylotrophic yeast, *Pelobacter, Vibrio, Halomonas, Pseudoalteromonas, Bacillus, Escherichia coli, Saccharomyces cerevisiae, Zymomonas mobilis, Cupriavidus basilensis, Corynebacterium glutamicum, Candida*, or any combination thereof.

In some embodiments, a microorganism is immobilized in the mineral clay surface up to $4.5\cdot10^{11}$ cells/g.

In some embodiments, the composition of the present invention has a zeta potential in the range of 15 mV to 0 mV.

In some embodiments, a microorganism is present in a ratio ranging from $1\cdot10^{11}$ to $4.5\cdot10^{11}$ cells/g of polycation attached to the mineral clay surface.

In some embodiments, the composition of the present invention has a zeta potential in the range of 20 mV to 0 mV.

In some embodiments, a microorganism is viable in a solution containing up to 4000 ppm aldehyde.

In some embodiments, a polycation has free amino groups.

In some embodiments, the composition of the present invention further comprises a solution of pH 3.5-4, or higher.

In some embodiments, the composition of the present invention is for use in reducing aldehyde concentration in a solution ranging from 5% to 100%.

In some embodiments, the composition of the present invention is for use in reducing aldehyde in a solution with a concentration of formaldehyde up to 8000 ppm.

In some embodiments, reducing aldehyde is adsorbing, degrading or both.

According to one aspect, there is provided a method for biodegradation of aldehyde, comprising adding the composition of the present invention to an aldehyde containing environment, thereby reducing the aldehyde concentration in the environment.

In some embodiments, reducing aldehyde concentration is by at least 50-100%.

In some embodiments, the method is for reducing aldehyde in a solution with a concentration of aldehyde up to 8000 ppm.

In some embodiments, reducing aldehyde is adsorbing, degrading or both.

In some embodiments, adding the composition of the invention to an aldehyde containing environment, is repeated up to 10 times.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 3A-D present graphs with the results of formaldehyde (FA) adsorption experiments; (FIG. 3A) Adsorption isotherm of FA on PEI-MMT composites at pH 9, (FIG. 3B) FA adsorption as a function of pH, (FIG. 3C) pH dependent FA desorption, (FIG. 3D) FTIR spectra of (a) MMT, (b) PEI-MMT composite and (c) PEI-MMT composite after FA adsorption (60 mg·g$^{-1}$);

FIGS. 7A-B present adsorption isotherms of PEI on MMT at different pH values (FIG. 7A) and scanning electron micrograph of a PEI-MMT composite prepared at pH 11.5 (300 mg PEI·g$^{-1}$ clay) (FIG. 7B);

DETAILED DESCRIPTION OF THE INVENTION

Figure 1:
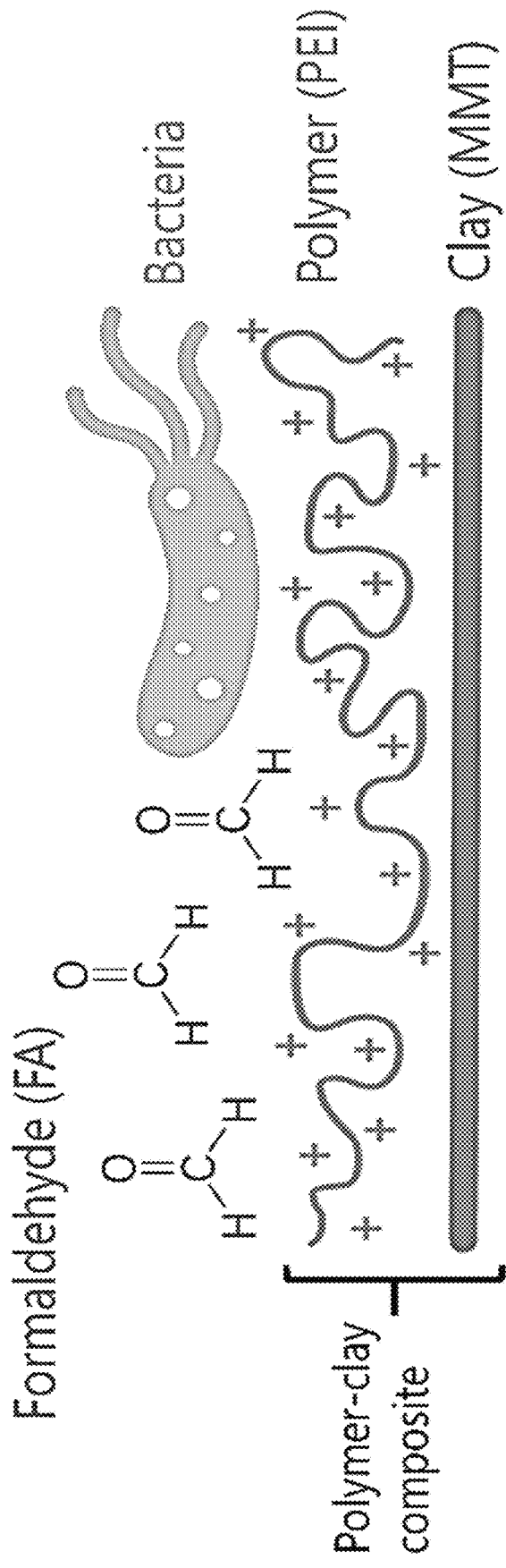
FIG. 1 presents a non-limiting schematic representation of a clay-polymer-formaldehyde degrading microorganism composite.

According to some embodiments, the present invention provides a composition comprising a mineral clay, at least one polycation attached to at least a portion of a surface of the mineral clay, and at least one aldehyde degrading microorganism.

According to some embodiments, the present invention provides a composition comprising a mineral clay, at least one polycation attached to at least a portion of a surface of the mineral clay, and at least one formaldehyde degrading microorganism.

The Composition

In some embodiments, a composition described herein is for use in reducing aldehyde from an aldehyde containing environment (e.g., solution). In some embodiments, a composition described herein is for use in adsorbing aldehyde from an aldehyde containing environment (e.g., solution). In some embodiments, a composition described herein is for use in degrading aldehyde from an aldehyde containing environment (e.g., solution). In some embodiments, a composition described herein is for use in adsorbing and degrading aldehyde from an aldehyde containing environment (e.g., solution).

In some embodiments, a composition described herein has a higher aldehyde adsorption rate than an aldehyde degrading rate. In some embodiments, the composition has an aldehyde adsorption rate at least 1 fold, at least 2 fold, at least 3 fold, at least 5 fold, at least 7 fold, at least 10 fold, at least 12 fold, at least 15 fold, at least 20 fold, at least 22 fold, or at least 25 fold higher than an aldehyde degrading rate.

In some embodiments, the composition reduces aldehyde levels from an aldehyde containing environment. The reduction of aldehyde levels makes the degradation of aldehyde possible. In some embodiments, the composition has a fast aldehyde adsorption capacity. In some embodiments, the composition is able to adsorb at least 50%, at least 60%, least 70%, at least 80%, least 850%, or at least 90%, of aldehyde from an aldehyde containing environment, within one minute.

As used herein, the term "aldehyde" refers to molecules having the formula RCHO. Aldehydes are characterized by the unsaturated carbonyl group (C=O). In some embodiments, the aldehyde is an aliphatic aldehyde. In some embodiments, the aldehyde is an aromatic aldehyde. In one embodiment, R group has a length of at least 1, 2, 3, 4, 5, 6, 7, 8, 9, 10, 11, 12, 13, 14, 15, 16, 17, 18, 19, or at least 20 carbons. R may be straight linear or branched. In some embodiments, a branched-chain has one or more branch points. Further, branched chain may include a cyclic branch. In some embodiments, R is saturated or unsaturated. If unsaturated, the R may have one or more unsaturated points. Non-limiting examples of aldehydes according to the present invention include formaldehyde, acetaldehyde, propanal, glyoxal, methylglyoxal, nonanal, decanal, benzaldehyde, furan aldehydes, acrolein, anis-aldehyde, and any combination thereof.

In some embodiments, a mineral clay surface is for use in adsorbing aldehyde from an aldehyde containing environment. In some embodiments, an aldehyde degrading microorganism is for use in degrading aldehyde from an aldehyde containing environment.

In some embodiments, a polycation from a composition described herein is for use in binding aldehyde covalently.

In some embodiments, an aldehyde comprises aldehyde comprises formaldehyde, acetaldehyde, propanal, glyoxal, methylglyoxal, nonanal, decanal, benzaldehyde, furan aldehydes, acrolein, anis-aldehyde, and any combination thereof. In some embodiments an aldehyde comprises formaldehyde.

In some embodiments, a composition described herein is for use in reducing formaldehyde from a formaldehyde containing environment (e.g., solution). In some embodiments, a composition described herein is for use in adsorbing formaldehyde from a formaldehyde containing environment (e.g., solution). In some embodiments, a composition described herein is for use in degrading formaldehyde from a formaldehyde containing environment (e.g., solution). In some embodiments, a composition described herein is for use in adsorbing and degrading formaldehyde from a formaldehyde containing environment (e.g., solution).

In some embodiments, a mineral clay surface is for use in adsorbing formaldehyde from a formaldehyde containing environment. In some embodiments, a formaldehyde degrading microorganism is for use in degrading formaldehyde from a formaldehyde containing environment.

In some embodiments, a polycation from a composition described herein is for use in binding formaldehyde covalently.

In some embodiments, a polycation from a composition described herein has free amino groups.

In some embodiments, a polycation from a composition described herein is for use in binding aldehyde covalently in a solution with a pH of more than about 3.5-4. In some embodiments, a polycation from a composition described herein is for use in binding aldehyde covalently in a solution with a pH of more than about 3.5. In some embodiments, a polycation from a composition described herein is for use in binding aldehyde covalently in a solution with a pH of more than about 4. In some embodiments, a polycation from a composition described herein is for use in binding aldehyde covalently in a solution with a pH of more than about 5. In some embodiments, a polycation form a composition described herein is for use in binding aldehyde covalently in a solution with a pH in a range of about 3.5-14, about, about 3.5-10, 4-14, about 4-10, about 5-14, about 5-10, or about 7-10, including any value and range therebetween.

In some embodiments, a composition as described herein is capable of elevate the pH of an aldehyde containing solution to a pH suitable for aldehyde degradation. In some embodiments, a composition as described herein is capable of elevate the pH of an aldehyde containing solution from 3.5 to 12, 3.5 to 10, 3.5 to 9, 3.5 to 8, 4 to 12, 4 to 10, 4 to 9, or 4 to 8, including any range therebetween.

In some embodiments, the binding of a polycation form a composition described herein to aldehyde is a reversible binding. In some embodiments, the binding of a polycation form a composition described herein to aldehyde is reversible binding at a pH lower than about 5, about 4, about 3, about 2, or about 1, including any value and range therebetween.

In some embodiments, a composition described herein further comprises a solution of pH 3.5 or higher. In some embodiments, a composition described herein further comprises a solution of pH 3.5-4 or higher. In some embodiments, a composition described herein further comprises a solution of pH 4 or higher. In some embodiments, a composition described herein further comprises a solution with a pH in a range of about 3.5-14, about 3.5-10, about 4-14, about 4-10, 5-14, about 5-10, about 5-11, about 7-10 or about 7-11, including any value and range therebetween.

In some embodiments, a composition described herein has a zeta potential in the range of about 50 mV to 0 mV, about 45 mV to 0 mV, about 40 mV to 0 mV, about 30 mV to 0 mV, about 20 mV to 0 mV, about 15 mV to 0 mV, or about 10 mV to 0 mV, including any value and range therebetween.

In some embodiments, a composition described herein is for use in reducing aldehyde concentration in a solution ranging from about 5% to 100%, about 10% to 100%, about 20% to 100%, about 30% to 100%, about 40% to 100%, about 50% to 100%, about 60% to 100%, about 70% to 100%, or about 80% to 100%, including any value and range therebetween.

In some embodiments, a composition described herein is for use in adsorbing aldehyde from an aldehyde containing solution. In some embodiments, a composition described herein is for use in adsorbing formaldehyde from a formaldehyde containing solution. In some embodiments, a composition described herein is able to adsorb about 62 mg formaldehyde (FA) per g of the total composition.

In some embodiments, a composition described herein is for use in adsorbing aldehyde, thereby reducing the concentration of aldehyde in a solution ranging from about 5% to 100%, about 10% to 100%, about 20% to 100%, about 30% to 100%, about 40% to 100%, about 50% to 100%, about 60% to 100%, about 70% to 100%, or about 80% to 100%, including any value and range therebetween. In some embodiments, a composition described herein is for use in adsorbing and degrading aldehyde, thereby reducing the concentration of aldehyde in a solution ranging from about 5% to 100%, about 10% to 100%, about 20% to 100%, about 30% to 100%, about 40% to 100%, about 50% to 100%, about 60% to 100%, about 70% to 100%, or about 80% to 100%, including any value and range therebetween.

In some embodiments, a composition described herein is for use in adsorbing formaldehyde, thereby reducing the concentration of formaldehyde in a solution ranging from about 5% to 100%, about 10% to 100%, about 20% to 100%, about 30% to 100%, about 40% to 100%, about 50% to 100%, about 60% to 100%, about 70% to 100%, or about 80% to 100%, including any value and range therebetween. In some embodiments, a composition described herein is for use in adsorbing and degrading formaldehyde, thereby reducing the concentration of formaldehyde in a solution ranging from about 5% to 100%, about 10% to 100%, about 20% to 100%, about 30% to 100%, about 40% to 100%, about 50% to 100%, about 60% to 100%, about 70% to 100%, or about 80% to 100%, including any value and range therebetween.

In some embodiments, a composition described herein is for use in reducing aldehyde in a solution with a concentration of aldehyde up to about 8000 ppm. In some embodiments, a composition described herein is for use in reducing aldehyde in a solution with a concentration of aldehyde ranging from about 0 to 8000 ppm, about 0 to 5000 ppm, about 0 to 3000 ppm, about 1000 to 8000 ppm, about 1000 to 5000 ppm, about 3000 to 8000 ppm, or about 5000 to 8000 ppm, including any value and range therebetween. In some embodiments, a composition described herein is for use in reducing formaldehyde in a solution with a concentration of formaldehyde up to about 8000 ppm. In some embodiments, a composition described herein is for use in reducing formaldehyde in a solution with a concentration of formaldehyde ranging from about 0 to 8000 ppm, about 0 to 5000 ppm, about 0 to 3000 ppm, about 1000 to 8000 ppm, about 1000 to 5000 ppm, about 3000 to 8000 ppm, or about 5000 to 8000 ppm, including any value and range therebetween.

As used herein, the term "reducing" refers to adsorbing, degrading or both.

Polymer-Clay Composites

In some embodiments, a polycation is attached to at least 25%, at least 30%, at least 35%, at least 40%, at least 45%, at least 50%, at least 55%, at least 60%, at least 65%, at least 70%, at least 75%, at least 80%, at least 85%, at least 90 at least 95%, or at least 99%, of the total mineral clay surface.

Examples of suitable polycations or polycationic materials include polyamines having amine groups on either the polymer backbone or the polymer side chains.

In some embodiments, the polycation has primary, secondary, tertiary amino groups in the polymer backbone or the polymer side chains or any combination thereof.

In some embodiments, "polycation" refers to one or more cationic polymers selected from the group consisting of polymers (e.g., having a molecular weight of 200 to 750,000) such as poly-L-arginine, poly-L-lysine, poly(ethylene glycol), polyethylenimine, chitosan, protamine, and the like. In some embodiments, the polycation is polyethylenimine (PEI).

As used herein, the term "polyethylenimine" or "PEI" refers to a cationic polymer having linear and branched chains and contains amino groups in the polymeric chain.

In some embodiments, the composition as described herein may comprise low loading of the polycation compound, e.g., concentration of up to about 0.5 mmol of compound per 1 gram of clay.

In some embodiments, the polycation (e.g., PEI) may be adsorbed to the external surface of the clay (e.g., MMT). In some embodiments, the polycation (e.g., PEI) may be adsorbed to the internal surface of the clay (e.g., MMT).

In some embodiments, a composition as described herein comprises high loading of the polycation compound, e.g., concentration of more than about 0.5 mmol of compound per 1 gram of clay.

In some embodiments, the PEI-MMT composite comprises at least 50 mg, at least 70 mg, at least 80 mg, at least 100 mg, at least 150 mg, at least 200 mg, at least 250 mg, or at least 300 mg, PEI/g of MMT.

In some embodiments, the PEI-MMT composite is prepared in a solution with a pH ranging from 7 to 12. In some embodiments, the PEI-MMT composite is prepared in a solution with a pH ranging from 7.5 to 11.5.

In some embodiments, the PEI-MMT composite is prepared in a solution with a pH of at least 7. In some embodiments, the PEI-MMT composite is prepared in a solution with a pH of at least 8. In some embodiments, the PEI-MMT composite is prepared in a solution with a pH of at least 9. In some embodiments, the PEI-MMT composite is prepared in a solution with a pH of at least 10. In some embodiments, the PEI-MMT composite is prepared in a solution with a pH of at least 11. In some embodiments, the PEI-MMT composite is prepared in a solution with a pH of at least 11.5.

As well understood in the art, segments of the adsorbed polymer are considered to belong one of three sequences; loops, tails and trains. Trains typically consist of groups of adjacent segments that are attached to the surfaces of the fine particles. Tails are typically the segments at the ends of the polymer that are not directly attached to the surfaces of the fine particles and extend out into the aqueous solution. Loops are typically intermediate sequences of segments, between trains and also extend into the aqueous solution.

In some embodiments, the polycation-clay composition is structurally based on the adsorption of any one of the compounds described herein (e.g., PEI) to the clay (e.g., MMT). By "adsorption" it is meant herein to refer to interactions between the compound and the clay.

In some embodiments, the interactions are of non-covalent nature. By "non-covalent nature" it is meant to refer to interaction selected from: hydrophobic, van der Waals and electrostatic interactions, as well as hydrogen bonding.

In exemplary embodiments, the adsorption of the polycation compound (e.g., PEI) on the clay (e.g., MMT) is mediated via van der Waals and/or electrostatic interactions.

In some embodiments, the adsorption of the polycation compound (e.g., PEI) on the clay (e.g., MMT) is mediated via electrostatic interactions between the positively charged amine groups from the polycation compound and the negatively charged clay.

In some embodiments, a composition as described herein comprises a positively charged amine. In some embodiments a composition as described herein comprises a positively charged primary amine, a positively charged secondary amine, a positively charged tertiary amine, a positively charged quaternary amine, or a combination thereof. Each possibility represents a separate embodiment of the present invention.

In some embodiments, the composition as described herein is positively charged.

In some embodiments, the positively charged amine is pH dependent.

By "positively charged" it is meant to refer to the polymeric backbone which contains chemical groups which carry, can carry, or can be modified so as to carry a positive charge.

In some embodiments, the composition-of-matter comprising polycation compound and clay remains substantially unaffected by the pH of the solution. For example, the composition-of-matter is positively charged at various values of pH ranging from about pH 2.5 to about pH 11, including any value therebetween.

Methods of the determining a charge of compositions are known in the art.

The charge of the composites described herein (i.e. PEI-MMT), may be determined by measuring the Zeta potential of aqueous suspension of the composites in various values of pH, showing Zeta potential values of e.g. +30 mV, +35 mV, +40 mV, +45 mV, +50 mV, +60 mV, +70 mV, +80 mV, including any value therebetween, depending on the concentration of the composite (e.g., PEI adsorbed in/on the MMT).

Immobilized Cell System

In some embodiments, a composition as described herein comprising at least one polycation attached to at least a portion of a surface of the mineral clay and at least one aldehyde degrading microorganism is referred to as cell-coated composites (termed ICS or Immobilized Cell System).

In some embodiments, an aldehyde degrading microorganism is selected from *Methylobacterium, Paecilomyces, Pseudomonas, Aspergillus, Ralstonia, Halomonas, Escherichia, Acetobacer, Klebsiella, Enterobacter, Corynebacterium*, methylotrophic yeast, Pelobacter, *Vibrio, Halomonas, Pseudoalteromonas, Bacillus, Escherichia coli, Saccharomyces cerevisiae, Zymomonas mobilis, Cupriavidus basilensis, Corynebacterium glutamicum, Candida*, or any combination thereof. In some embodiments, an aldehyde degrading microorganism is *P. putida* NS15.

In some embodiments, an aldehyde degrading microorganism is a formaldehyde degrading microorganism.

As used herein, the term "aldehyde degrading microorganism" refers to any natural occurring microorganism or recombinant microorganism having an aldehyde degrading activity. In some embodiments, an aldehyde degrading microorganism is a microorganism having aldehyde dismutase activity, aldehyde dehydrogenase activity, oxidoreductase activity, or any other known aldehyde-degrading enzymatic activity. In some embodiments, an aldehyde degrading microorganism is a microorganism having aldehyde dehydrogenase activity. In some embodiments, an aldehyde degrading microorganism is a microorganism having aldehyde dismutase activity. As used herein, the term "formaldehyde degrading microorganism" refers to any natural occurring microorganism or recombinant microorganism having a FA degrading activity. In some embodiments, a formaldehyde degrading microorganism is a microorganism having aldehyde dismutase activity, aldehyde dehydrogenase activity, oxidoreductase activity, or any other known FA-degrading enzymatic activity. In some embodiments, a formaldehyde degrading microorganism is a microorganism having formaldehyde dehydrogenase activity. In some embodiments, a formaldehyde degrading microorganism is a microorganism having formaldehyde dismutase activity.

In some embodiments, an aldehyde degrading microorganism is immobilized in a mineral clay surface up to about $4.5 \cdot 10^{11}$ cells/g, about $4 \cdot 10^{11}$ cells/g, about $3 \cdot 10^{11}$ cells/g, about $2 \cdot 10^{11}$ cells/g, about $1 \cdot 10^{11}$ cells/g, about $1 \cdot 10^{10}$ cells/g, about $1 \cdot 10^{9}$ cells/g, or about $1 \cdot 10^{8}$ cells/g, including any value and range therebetween. In some embodiments, a formaldehyde degrading microorganism is immobilized in a mineral clay surface up to about $4.5 \cdot 10^{11}$ cells/g, about $4 \cdot 10^{11}$ cells/g, about $3 \cdot 10^{11}$ cells/g, about $2 \cdot 10^{11}$ cells/g, about $1 \cdot 10^{11}$ cells/g, about $1 \cdot 10^{10}$ cells/g, about $1 \cdot 10^{9}$ cells/g, or about $1 \cdot 10^{8}$ cells/g, including any value and range therebetween.

In some embodiments, the immobilization of a microorganism is optimal when the zeta potential of the composition as described herein is between about 20-0 mV, about 19-0 mV, about 18-0 mV, about 17-0 mV, about 16-0 mV, about 15-0 mV, about 14-0 mV, about 13-0 mV, about 12-0 mV, about 11-0 mV, or about 10-0 mV, including any value and range therebetween.

In some embodiments, immobilized refers to attachment to a surface, forming a layer on a surface, ionic interactions, electrostatic interactions or any combination thereof.

In some embodiments, the microorganism is immobilized on the surface by interacting electrostatically with an available amino group of a polycation of the composition as described herein.

In some embodiments, a microorganism immobilized according to the present invention has a higher aldehyde degrading capacity when compared to free cells of the microorganism.

In some embodiments, a microorganism immobilized according to the present invention is active in an aldehyde containing environment for a longer period of time when compared to free cells of the microorganism.

In some embodiments, a microorganism immobilized according to the present invention retains its activity and is able to continuously remove aldehyde from an aldehyde containing environment for a longer period when compared to free cells of the microorganism.

In some embodiments, a microorganism is present in a ratio ranging from about $1 \cdot 10^{3}$ to $4.5 \cdot 10^{11}$ cells/g of polycation attached to the mineral clay surface. In some embodiments, a microorganism is present in a ratio ranging from about $1 \cdot 10^{5}$ to $4.5 \cdot 10^{11}$ cells/g, about $1 \cdot 10^{7}$ to $4.5 \cdot 10^{11}$ cells/g, about $1 \cdot 10^{8}$ to $4.5 \cdot 10^{11}$ cells/g, about $1 \cdot 10^{10}$ to $4.5 \cdot 10^{11}$ cells/g, about $1 \cdot 10^{11}$ to $4.5 \cdot 10^{11}$ cells/g, about $1.5 \cdot 10^{11}$ to $4.5 \cdot 10^{11}$ cells/g, about $2 \cdot 10^{11}$ to $4.5 \cdot 10^{11}$ cells/g, about $2.5 \cdot 10^{11}$ to $4.5 \cdot 10^{11}$ cells/g, about $3 \cdot 10^{11}$ to $4.5 \cdot 10^{11}$ cells/g, about $3.5 \cdot 10^{11}$ to $4.5 \cdot 10^{11}$ cells/g, or about $4 \cdot 10^{11}$ to $4.5 \cdot 10^{11}$ cells/g, including any value and range therebetween. Each possibility represents a separate embodiment of the present invention.

In some embodiments, a microorganism is viable in a solution containing up to about 4000 ppm aldehyde. In some embodiments, a microorganism is viable in a solution containing up to about 3900 ppm, about 3800 ppm, about 3700 ppm, about 3600 ppm, about 3500 ppm, about 3400 ppm, to about 3300 ppm, about 3200 ppm, about 3100 ppm, about 2900 ppm, about 2800 ppm, about 2700 ppm, about 2600 ppm, about 2500 ppm, about 2400 ppm, about 2300 ppm, about 2100 ppm, or about 2000 ppm aldehyde, including any value and range therebetween. Each possibility represents a separate embodiment of the present invention. In some embodiments, a microorganism is viable in a solution containing up to about 4000 ppm formaldehyde. In some embodiments, a microorganism is viable in a solution containing up to about 3900 ppm, about 3800 ppm, about 3700 ppm, about 3600 ppm, about 3500 ppm, about 3400 ppm, to about 3300 ppm, about 3200 ppm, about 3100 ppm, about 2900 ppm, about 2800 ppm, about 2700 ppm, about 2600 ppm, about 2500 ppm, about 2400 ppm, about 2300 ppm, about 2100 ppm, or about 2000 ppm formaldehyde, including any value and range therebetween. Each possibility represents a separate embodiment of the present invention.

As used herein the term "viable" refers to the ability of a microorganism or culture to degrade formaldehyde in a formaldehyde containing solution. In some circumstances, a viable culture is not capable of growing well or at all, but is still capable of degrading formaldehyde from a solution. A "non-viable" microorganism or culture is comprised of cells that are either dead or sufficiently damaged that they are no longer capable of degrading formaldehyde in a formaldehyde containing solution.

In some embodiments, a microorganism is viable when used in an aldehyde containing solution for at least 2, at least 3, at least 4, at least 5, at least 6, at least 7, at least 8, at least 9, or at least 10, consecutive cycles.

In some embodiments, a microorganism preserves at least 80% of its activity when used in an aldehyde containing solution for at least 2, at least 3, at least 4, at least 5, at least 6, at least 7, at least 8, at least 9, or at least 10, consecutive cycles. In some embodiments, a microorganism preserves at least 90% of its activity when used in an aldehyde containing solution for at least 2, at least 3, at least 4, at least 5, at least 6, at least 7, at least 8, at least 9, or at least 10, consecutive cycles. In some embodiments, a microorganism preserves at least 95% of its activity when used in an aldehyde containing solution for at least 2, at least 3, at least 4, at least 5, at least 6, at least 7, at least 8, at least 9, or at least 10, consecutive cycles.

The Method

According to some embodiments, the present invention provides a method for biodegradation of aldehyde, comprising adding a composition as described herein to an aldehyde containing environment, thereby reducing the aldehyde concentration in an environment.

Aldehyde according to the present invention has been described elsewhere herein. Non-limiting examples of aldehydes according to the present invention include formaldehyde, acetaldehyde, propanal, glyoxal, methylglyoxal, nonanal, decanal, and any combination thereof.

In some embodiments, an aldehyde comprises aldehyde comprises formaldehyde, acetaldehyde, propanal, glyoxal, methylglyoxal, nonanal, decanal, benzaldehyde, furan aldehydes, acrolein, anis-aldehyde, and any combination thereof. In some embodiments an aldehyde comprises formaldehyde.

According to some embodiments, the present invention provides a method for biodegradation of formaldehyde, comprising adding a composition as described herein to a formaldehyde containing environment, thereby reducing the formaldehyde concentration in an environment. In some embodiments, an aldehyde containing environment is a solution. In some embodiments, an aldehyde containing environment is wastewaters.

In some embodiments, a method as described herein is able of reducing aldehyde concentration ranging from about 5% to 100%, about 10% to 100%, about 20% to 100%, about 30% to 100%, about 40% to 100%, about 50% to 100%, about 60% to 100%, about 70% to 100%, or about 80% to 100%, including any value and range therebetween. In some embodiments, a method as described herein is able of reducing formaldehyde concentration ranging from about 5% to 100%, about 10% to 100%, about 20% to 100%, about 30% to 100%, about 40% to 100%, about 50% to 100%, about 60% to 100%, about 70% to 100%, or about 80% to 100%, including any value and range therebetween.

In some embodiments, a method as described herein is capable of reducing aldehyde in a solution with a concentration of aldehyde up to about 8000 ppm. In some embodiments, a method as described herein is capable of reducing aldehyde in a solution with a concentration of aldehyde ranging from about 0 to 8000 ppm, about 0 to 5000 ppm, about 0 to 3000 ppm, about 1000 to 8000 ppm, about 1000 to 5000 ppm, about 3000 to 8000 ppm, or about 5000 to 8000 ppm, including any value and range therebetween. In some embodiments, a method as described herein is capable of reducing formaldehyde in a solution with a concentration of formaldehyde up to about 8000 ppm. In some embodiments, a method as described herein is capable of reducing formaldehyde in a solution with a concentration of formaldehyde ranging from about 0 to 8000 ppm, about 0 to 5000 ppm, about 0 to 3000 ppm, about 1000 to 8000 ppm, about 1000 to 5000 ppm, about 3000 to 8000 ppm, or about 5000 to 8000 ppm, including any value and range therebetween.

In some embodiments, a method as described herein is capable of reducing aldehyde from an aldehyde containing solution. In some embodiments, a method as described herein is capable of adsorbing aldehyde from an aldehyde containing solution. In some embodiments, a method as described herein is capable of degrading aldehyde from an aldehyde containing solution. In some embodiments, a method as described herein is capable of adsorbing and degrading aldehyde from an aldehyde containing solution.

In some embodiments, a method as described herein is capable of adsorbing aldehyde, thereby reducing the concentration of aldehyde in a solution ranging from about 5% to 100%, about 10% to 100%, about 20% to 100%, about 30% to 100%, about 40% to 100%, about 50% to 100%, about 60% to 100%, about 70% to 100%, or about 80% to 100%, including any value and range therebetween. In some embodiments, a method as described herein is capable of adsorbing formaldehyde, thereby reducing the concentration of formaldehyde in a solution ranging from about 5% to 100%, about 10% to 100%, about 20% to 100%, about 30% to 100%, about 40% to 100%, about 50% to 100%, about 60% to 100%, about 70% to 100%, or about 80% to 100%, including any value and range therebetween.

In some embodiments, a method as described herein is capable of adsorbing and degrading aldehyde, thereby reducing the concentration of aldehyde in a solution ranging from about 5% to 100%, about 10% to 100%, about 20% to 100%, about 30% to 100%, about 40% to 100%, about 50% to 100%, about 60% to 100%, about 70% to 100%, or about 80% to 100%, including any value and range therebetween. In some embodiments, a method as described herein is capable of adsorbing and degrading formaldehyde, thereby reducing the concentration of formaldehyde in a solution ranging from about 5% to 100%, about 10% to 100%, about 20% to 100%, about 30% to 100%, about 40% to 100%, about 50% to 100%, about 60% to 100%, about 70% to 100%, or about 80% to 100%, including any value and range therebetween.

According to some embodiments, the present invention provides a method for biodegradation of aldehyde in wastewaters, comprising adding up to 40 g/L of a composition as described herein to wastewaters, thereby reducing the aldehyde concentration in wastewaters. According to some embodiments, the present invention provides a method for biodegradation of formaldehyde in wastewaters, comprising adding up to 40 g/L of a composition as described herein to wastewaters, thereby reducing the formaldehyde concentration in wastewaters.

In some embodiments, a method as described herein comprises adding about 10 mg/L, about 50 mg/L, about 100 mg/L, about 200 mg/L, about 500 mg/L, about 800 mg/L, about 1 g/L, about 10 g/L, about 20 g/L, about 30 g/L, or about 40 g/L, including any value and range therebetween, a composition as described herein to wastewaters, thereby reducing the aldehyde concentration in wastewaters. In some embodiments, a method as described herein comprises adding about 10 mg/L, about 50 mg/L, about 100 mg/L, about 200 mg/L, about 500 mg/L, about 800 mg/L, about 1 g/L, about 10 g/L, about 20 g/L, about 30 g/L, or about 40 g/L, including any value and range therebetween, a composition as described herein to wastewaters, thereby reducing the formaldehyde concentration in wastewaters.

In some embodiments, adding the composition to an aldehyde containing solution is repeated up to 10 times. In some embodiments, the composition is added to the aldehyde containing environment at least 1 time, at least 2 times, at least 3 times, at least 4 times, at least 5 times, at least 6 times, at least 7 times, at least 8 times, at least 9 times, or at least 10 times.

In some embodiments, the microorganism is viable when used in an aldehyde containing solution for at least 2, at least 3, at least 4, at least 5, at least 6, at least 7, at least 8, at least 9, or at least 10, consecutive cycles.

In some embodiments, at least 80% of the degradation efficiency is maintained when used in an aldehyde containing solution for at least 2, at least 3, at least 4, at least 5, at least 6, at least 7, at least 8, at least 9, or at least 10, consecutive cycles. In some embodiments, at least 90% of the degradation efficiency is maintained when used in an aldehyde containing solution for at least 2, at least 3, at least 4, at least 5, at least 6, at least 7, at least 8, at least 9, or at least 10, consecutive cycles. In some embodiments, at least 95% of the degradation efficiency is maintained when used in an aldehyde containing solution for at least 2, at least 3, at least 4, at least 5, at least 6, at least 7, at least 8, at least 9, or at least 10, consecutive cycles.

In some embodiments, at least 80% of the adsorption efficiency is maintained when used in an aldehyde containing solution for at least 2, at least 3, at least 4, at least 5, at least 6, at least 7, at least 8, at least 9, or at least 10, consecutive cycles. In some embodiments, at least 90% of the adsorption efficiency is maintained when used in an aldehyde containing solution for at least 2, at least 3, at least 4, at least 5, at least 6, at least 7, at least 8, at least 9, or at least 10, consecutive cycles. In some embodiments, at least 95% of the adsorption efficiency is maintained when used in an aldehyde containing solution for at least 2, at least 3, at least 4, at least 5, at least 6, at least 7, at least 8, at least 9, or at least 10, consecutive cycles.

In some embodiments, at least 80% of the degradation efficiency and adsorption efficiency is maintained when used in an aldehyde containing solution for at least 2, at least 3, at least 4, at least 5, at least 6, at least 7, at least 8, at least 9, or at least 10, consecutive cycles. In some embodiments, at least 90% of the degradation efficiency and adsorption efficiency is maintained when used in an aldehyde containing solution for at least 2, at least 3, at least 4, at least 5, at least 6, at least 7, at least 8, at least 9, or at least 10, consecutive cycles. In some embodiments, at least 95% of the degradation efficiency and adsorption efficiency is maintained when used in an aldehyde containing solution for at least 2, at least 3, at least 4, at least 5, at least 6, at least 7, at least 8, at least 9, or at least 10, consecutive cycles.

Definitions

As used herein, the term "formaldehyde" or "FA" refers to a compound of the general formula $CH_2O$, having the CAS number 50-00-0. It also known to the skilled artisan as formalin, methylene oxide, methyl aldehyde, methanal, HCHO, formic aldehyde, oxomethane, formol, oxymethylene, morbicid, veracur, methylene glycol, formalin 40, BFV, fannoform, formalith, FYDE, HOCH, karsan, lysoform, superlysoform, methan 21. In pure form, formaldehyde is a gas but is often used in liquid form after diluting with water as the hydrate $HO—(CH_2O)_n—H$ known as methandiol. Aqueous solutions of formaldehyde are referred to as formalin. It is a colorless highly flammable liquid or gas with a pungent odor that is detectable at 1 part per million (ppm). Formaldehyde mixtures (e.g. mixtures with water, acetone, benzene, diethyl ether, chloroform and ethanol) are included for the purposes of the present invention as well. Polymers of formaldehyde encompassed in the present definition include low and high molecular mass polymers, in particular paraformaldehyde, as well as linear and cyclic polyoxymethylenes.

As used herein, the term "clay" refers to the group consisting of: mineral clays, synthetic clays, organoclays and any mixture(s) thereof.

In some embodiments of the present invention the clay is a mineral clay.

As used herein, the term "mineral clay" refers to a naturally occurring or synthetic material composed primarily of fine-grained minerals (e.g., aluminosilicates) that show plasticity through a variable range of water content (which may be a result of water trapped in the structure by polar attraction) and can be hardened when dried and/or fired.

These clay minerals are characterized by a mineral structure formed by the arrangement of octahedral units and tetrahedral units or by stacked layers formed by an octahedral sheet and one or more tetrahedral sheets of the atoms that constitute the clay mineral structure.

Exemplary mineral clays include, but are not limited to, illite, phyllosilicate, Montmorillonite, kaolinite, illite, sepiolite, attapulgite, hectoritebentonite, zeolite, aluminosilicate, montmorillonite (MMT), smectite, and kaolinite.

In exemplary embodiments of the present invention the clay is Montmorillonite (e.g., bentonite, macaloid, or any combination, derivative or analogue thereof).

As used herein, the term "organoclay" and the term "modified clay" refer to an organically modified phyllosilicate, derived from a naturally occurring clay mineral. By exchanging the original interlayer cations for organocations or polysaccharides, an organophilic surface is generated. The lamellar structure remains analogous to the parent phyllosilicate.

As used herein, the term "wastewater" and "WW" and "effluent water", may be used interchangeably to refer to any solution that has water as a primary component and is a discharge or effluent that includes one or more contaminants. "Wastewater" refers to any residuals stream that may contain solid or biosolid material, such as from a sewage treatment operation. Any volumetric flow rate may enter the wastewater treatment system, for example, an average flow rate of about 1000 gal/min, about 500 gal/min, or about 100 gal/min. The flow rate of fluid into the treatment system may be steady, periodic, or irregular, depending on the application. Other flow rates may be necessary in certain cases. In some cases, the fluid may first be collected into a holding vessel to, for example, control or regulate the flow of fluid through the treatment system, or dampen irregularities in the flow rate. Any holding vessel suitable for containing or storing the fluid may be used. As used herein, a "fluid" generally refers to a substance having flow properties, including slurries, semi-solid systems, or liquids containing solid or suspended components.

As used herein the term "zeta potential" refers to a scientific term for electrokinetic potential in colloidal systems. In the colloidal chemistry literature, it is usually denoted using the Greek letter zeta, hence $\zeta$-potential. Zeta potential is a measure of the magnitude of the repulsion or attraction between particles. Zeta potential is an index of the magnitude of interaction between colloidal particles and measurements of zeta potential are used to access the stability of colloidal systems.

In aqueous media, the pH of the sample affects its zeta potential. For example, if alkali is added to a suspension with a negative zeta potential the particles tend to acquire more negative charge. If sufficient acid is added to the suspension, then a point will be reached where the charge will be neutralized. Further addition of acid will cause a buildup of positive charge.

In some embodiments, a composition as described herein has a zeta potential at 25° C. In some embodiments, a composition as described herein has a zeta potential in the range of about 0.5 to 100 mV or about −0.5 to −100 mV. In some embodiments the zeta potential is in the range of about 1 to 60 mV or about −1 to −60 mV, about 14 to 50 mV or about −14 to −50 mV, about 30 to 50 mV or about −30 to −50 mV. In some embodiments the zeta potential is in the range of about 0.5 to 100 mV or about −0.5 to −100 mV, about 1 to 60 mV or about −1 to −60 mV, about 14 to 50 mV or about −14 to −50 mV, about 30 to 50 mV or about −30 to −50 mV.

As used herein, the term "microorganism" refers to any organism or combination of organisms of microscopic size, to a single-celled organism, and/or to any virus particle such as bacteria, viruses, protozoa, yeasts, fungi, molds, or spores formed by any of these.

Articles

According to an aspect of some embodiments of the present invention there is provided an article (e.g., an article-of-manufacturing) incorporating in and/or on at least a portion thereof the composite or composition-of-matter described in any one of the respective embodiments hereinabove.

The article can be any article which can benefit from the composite or the composition-of-matter as described herein for the removal or preventing of organic-based pollutant in aqueous solution.

Exemplary articles include, but are not limited to, organic waste processing device, fluidic device, an agricultural device, a package, a sealing article, a fuel container, water and/or cooling system device and a construction element.

Non-limiting examples of devices which can incorporate the hybrid or the composition-of-matter as described herein, beneficially, include tubing, pumps, drain or waste pipes, screw plates, and the like.

In some embodiments, the article is an element used in water treatment systems (such as for containing, transporting, or treating aqueous media or water), devices, containers, filters, tubes, solutions and gases and the likes.

In some embodiments, the article is an element in organic waste treatment systems (such as for containing, disposing, transporting, or treating organic waste), devices, containers, filters, tubes, chromatographic purification platforms (e.g., packed columns) and the likes.

Other exemplary embodiments include, but are not limited to, containers, storage tanks, raw milk holding equipment, dairy processing operations conveyer belts, tube walls, gaskets, rubber seals, stainless steel coupons, piping systems, filling machine, silo tanks, heat exchangers, post-pasteurization equipment, pumps, valves, separators, and spray devices.

General

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials

Branched polyethylenimine (750 kDa, 50% w/w aqueous solution) was purchased from Sigma Aldrich. The $pK_a$ of PEI was determined as 10.9 by zeta potential measurements. Wyoming Na-montmorillonite (SWy-3) was obtained from the Source Clays Repository of the Clay Minerals Society (Columbia, Mo.). Fordor, a synthetic 36.5% (±1%) FA solution containing 3%-5% methanol as an anti-polymerization agent, and wastewater samples (pH 3.6, 50,000 ppm FA) from the production of urea-formaldehyde resin were supplied by Dor Chemicals Ltd.

Composite Preparation and Characterization

Adsorption isotherms. PEI adsorption on MMT was tested at pH 7.6, 9 and 11. The pH of PEI stock solutions was adjusted using a 32% v/v HCl solution. 5 mL of MMT suspension (5 g/L) were mixed with 10 mL of PEI solutions to reach final concentrations of 0.05 to 5 g·L$^{-1}$ PEI and 1.67 g·L$^{-1}$ MMT (15 mL in 50 mL centrifuge tubes, the experiment was conducted triplicates for each concentration). The samples were agitated for two hours (equilibrium of PEI was established after 1 hour) and centrifuged at 6000 rpm for 10 minutes. Equilibrium concentration of PEI in the supernatant solutions was determined through the colorimetric reaction of PEI with copper sulfate, detectable at a wavelength of 272 nm. Briefly, 2 mL of PEI solution were mixed with 100 μL of CuSO$_4$ 20 mM before measuring the absorbance in a Genesys 10S UV-Vis spectrophotometer (Thermo Scientific).

The composite used in later experiments was prepared using 3 g·L$^{-1}$ PEI and 5 g·L$^{-1}$ MMT. The elevated concentrations resulted in a higher ambient pH (11.5) and produced composites with a PEI loading of 300 mg/g clay. Unless stated otherwise, the composite was washed with deionized water to remove excess PEI; composite weights given are the calculated weights of dry matter within composite pellets.

Desorption of PEI from the prepared composite (300 mg·g$^{-1}$) was tested in saline (8.5 g·L$^{-1}$ NaCl), to match the conditions of later biotic experiments. Washed composite pellets were suspended in saline at ambient pH (10.2) or adjusted with 1 M HCl to pH 4, 7 or 9. The suspended composites were agitated for 1 hour and the PEI content of the supernatants was measured using CuSO$_4$. To negate pH effects on the PEI-Cu reaction, the supernatants were mixed with an equal volume of acetate buffer (200 mM, pH 4.85) before adding copper. The PEI-Cu reaction was not significantly affected at this ionic strength.

X-ray diffraction (XRD) measurements. Oriented samples of MMT and PEI-MMT composites (70-300 mg PEI/g clay, made at pH 7.6-11.5) were prepared by placing 100-200 μL of suspended material on glass slides and allowing them to sediment. Basal spacing was measured using a Philips PW1820 X-ray diffractometer with Cu Kα radiation (λ=1.540 Å).

Zeta potential measurements. The zeta potential of MMT, PEI-MMT composites, and composites carrying FA-degrading bacteria was measured after appropriate dilution in deionized water, using a Zetasizer Nano ZS (Malvern Instruments, UK). Sample suspensions were left undisturbed for 5 minutes before collecting 1 mL from the topmost layer for measurement.

Confocal microscopy. The composite (300 mg PEI·g$^{-1}$ clay) was suspended in saline and examined in a confocal laser scanning microscope (Leica TCS SP8, Leica Microsystems, Wetzlar, Germany) using ×25 magnification.

FA Binding
Quantification

FA adsorption and desorption experiments. The effect of pH for FA adsorption was determined at a composite concentration of 5.7 g·L$^{-1}$ (300 mg PEI·g$^{-1}$ clay) and 650 ppm FA, using amine-free buffers at pH 3·10. 15 mL of buffered FA solution were added to 98 mg composite in 50 mL centrifuge tubes. The tubes were agitated 1.5 hours, centrifuged 12 minutes at 6000 rpm, and the FA content of the supernatants was used to calculate the adsorbed amount of FA. FA concentrations in aqueous solutions were determined spectrophotometrically using Nash reagent. Briefly, 20 μL of FA solution were added to a test tube containing 2 mL of Nash reagent and incubated in a dry bath at 60° C. for 10 minutes. The reaction products were cooled in icy water before measuring the absorbance at 412 nm.

1) Adsorption kinetics were studied over the course of 48 hours by agitating 98 mg composite in 15 mL buffered FA solution (840 ppm, pH 8.8) with separate triplicates for selected time points. To account for FA evaporation during agitation, control tubes containing only FA solution were set for each time point, and adsorption was calculated as the difference between FA concentration in experimental and control tubes.

2) Adsorption kinetics were studied by incubating 60 mg of the composite in 9 mL FA solution (320-770 ppm), in duplicates for each time point. The reaction was stopped by filtering the composite suspension through a 0.22 μm membrane before measuring the residual FA in the filtrate. The kinetics of FA adsorption were modelled using the pseudo-first order and pseudo-second order equations:

$$q = q_e - q_e \cdot \exp(-k \cdot t) \tag{1}$$

$$q = \frac{k \cdot q_e^2 \cdot t}{1 + k \cdot q_e \cdot t} \tag{2}$$

Where q is the amount of adsorbed FA (mg·g$^{-1}$ composite) at time t (min), $q_e$ is the adsorbed amount at equilibrium, k is the rate constant (min-1 for first order and g·mg$^{-1}$·min$^{-1}$ for second order); Equation (1) was used to model 1$^{st}$ order kinetics and Eq. (2) was used for 2$^{nd}$ order.

The binding isotherm of FA to the PEI-MMT composite was obtained using 5.7 g·L$^{-1}$ composite and 0-1100 ppm FA. Because the reaction of FA with amines affects the pH as it evolves, FA solutions were brought to pH 10 with NaOH 0.25M before use, reaching a final pH of ~9 when mixed with the composite. Release experiments were conducted by washing the composite for 1.5 hours in deionized water at pH 2, 4, 7, and 9. The pH was adjusted individually in each tube using HCl 0.25M and NaOH 50 mM solutions to account for the composite's buffering capacity. Adsorption data were fitted to the Langmuir adsorption isotherm (Eq. 3):

$$q = \frac{q_{max} \cdot k_L \cdot C}{1 + k_L \cdot C} \tag{3}$$

q is the adsorbed FA (mg·g$^{-1}$), qmax is the adsorption capacity, kL is the Langmuir coefficient (L·mg$^{-1}$), and C is the concentration of FA in the solution.

Adsorption from wastewater "WW". FA removal from WW was studied at 32.5 g composite·L$^{-1}$ and 5000 ppm FA. 3.25 g freeze dried composite were weighed into 100-mL screw cap bottles and added 90 mL of deionized water and 10 mL WW. The mixture was set on a magnetic stirrer for 1.5 hours before collecting 2-mL aliquots to determine residual FA concentrations. The experiment was carried out in duplicates.

Fourier transform infrared (FTIR) spectroscopy. FTIR spectra of PEI, MMT and PEI-MMT composites before and after FA adsorption were recorded at room temperature in the range of 400-4000 cm$^{-1}$ on a Thermo Scientific Nicolet iS50 spectrometer. The spectrum of PEI was measured from an aqueous solution with a deionized water sample as the reference (blank) using ATR-FTIR. All other samples were vacuum dried, ground to a fine powder with KBr and pressed into pellets approximately 1 mm thick. Measurements were conducted with a KBr pellet as reference.

FA-Degrading Bacteria

Bacterial strains. FA-degrading bacteria were isolated from agricultural soils by plating soil suspensions on agar with FA as a sole carbon source. 16S rDNA genes of individual colonies were amplified using the primers 27F (5'-GAGAGTTTGATCCTGGCTCAG-3') (SEQ ID NO: 1) and 1495R (5'-CTACGGCTACCTTGTTACGA-3') (SEQ ID NO: 2). Sequences were identified using nucleotide BLAST. A *Pseudomonas fluorescens* strain expressing green fluorescent protein (GFP) was used as a non-FA degrading control strain.

Growth conditions. GFP-expressing *P. fluorescens* was grown under aerobic conditions at 30° C., in Luria Bertani medium supplemented with 25 μg·mL$^{-1}$ kanamycin (LBK). FA-degrading strains were grown under aerobic conditions at 30° C. in minimal salts medium (MM) comprised of 50 mM Tris-HCl buffer (pH 8), 0.1 g·L$^{-1}$ yeast extract, 2 g·L$^{-1}$ (NH$_4$)$_2$SO$_4$, 0.351 g·L$^{-1}$ KH$_2$PO$_4$, 0.073 g·L$^{-1}$ MgSO$_4$, 0.624 mg·L$^{-1}$ CuSO$_4$.5H$_2$O, 6.039 mg·L$^{-1}$ FeSO$_4$.7H$_2$O, 0.45 mg·L$^{-1}$ MnSO$_4$.H$_2$O, 0.423 mg·L$^{-1}$ ZnSO$_4$.7H$_2$O, 0.789 mg·L$^{-1}$ CoCl$_2$.6H$_2$O, 0.696 mg·L$^{-1}$ NaMoO$_4$.2H$_2$O and 3.681 g·L$^{-1}$ CaCl$_2$.2H$_2$O. MM was nominally enriched with 0.1% w/w glucose and 925 ppm FA (MM-FDG 0.1%). Unless stated otherwise, bacteria were grown to the exponential growth phase, harvested by centrifugation (10 minutes at 8000 g, room temperature) and washed (40 mL/100 mL culture) before use with 50 mM pH 8 Tris-HCl buffer or saline (8.5 g·L$^{-1}$ NaCl). Microbial growth was monitored by measuring the optical density (OD) of the culture at 600 nm in a microplate reader. Experiments were conducted in triplicates.

FA biodegradation rates. 1) Bacteria were grown overnight in MM-FDG 0.1%. The cells were harvested by centrifugation, washed with Tris-HCl buffer and resuspended to an OD of 2.0 in a similar buffer solution containing 370 ppm FA. 12 mL test tubes holding 3 mL culture were incubated at 30° C. and 250 rpm for 4 hours, during which samples were drawn at selected time points for FA analysis as described above. The fastest degrader, a variant of *Pseudomonas putida* named *P. putida* NS15, was chosen for further research.

2) Bacteria was grown overnight in MM-FDG 0.1%. The cells were harvested by centrifugation, washed and suspended in saline or 100 mM pH 8 phosphate buffer. 2 mL of cell suspension were added to 20 mL glass vials holding 2 mL FA solution, to give final concentrations of 370-770 ppm FA and OD 2.0. The vials were incubated at 30° C. and 250 rpm. Two vials were sacrificed at selected time points, and the suspension was filtered through a 0.22 μm membrane for FA analysis. Biodegradation kinetics were modelled using Eq. (4) and (5) for the pseudo-first and pseudo-second rate order, respectively:

$$A = A_0 e^{-kt} \quad (4)$$

$$\frac{1}{A} = \frac{1}{A_0} + kt \quad (5)$$

Where A is the amount of degraded FA (ppm) at time t (min), Ao is the initial FA concentration and k is the rate constant (min-1 for first order and ppm·min-1 for second order).

Total organic carbon (TOC) was measured and compared to the FA removal profile at several time points during FA biodegradation. Measurements were taken using a TOC-VCPH analyzer (Shimadzu) after filtration and acidification of the samples.

Bacterial tolerance of pH and FA. The growth of *P. putida* NS15 at several pH values and FA concentrations was tracked for 16 hours in a microplate reader. FA tolerance was tested in MM containing 0.05% glucose and 550 to 9000 ppm FA. pH tolerance was examined at pH 5-10.6 in MM containing 0.05% glucose, 925 ppm FA and 5% of different buffers (phosphate-citrate buffers at pH 5 and 6.6, Tris-HCl buffer at pH 8, and glycine-NaOH buffers at pH 9.3 and 10.6). Buffers were not found to significantly alter FA concentration. Media were inoculated with unwashed cell culture to a similar initial OD 0.008.

Immobilization

Cell adsorption isotherm. *P. putida* NS15, harvested as described above, was suspended in saline to OD 1.1 and serially diluted to create cell suspensions at ODs ranging from 0.14 to 1.1. 8 mL of each suspension were added in triplicate to 2 mL composite suspension (final concentration 0.55 g·L$^1$) in 27 mL glass vials. Vials were agitated for one hour to reduce aggregation and allowed to settle for two hours before carefully collecting the top 1 mL. Cell loading was calculated based on the turbidity of the collected supernatant. The resulting cell-coated composites (termed ICS for *Immobilized Cell System*) (FIG. 1) were washed in saline to remove unbound cells before measuring their zeta potential to ensure no unbound cells were sampled with the ICS.

Scanning electron microscopy (SEM) imaging. 100 μL of suspended PEI-MMT composite with or without immobilized *P. putida* NS15 (2.5·10$^{11}$ cells·g$^{-1}$) were fixed on glass slides using 2.5% glutaraldehyde in phosphate-buffered saline (10 mM, pH 7.4) for two hours. The specimens were washed in an increasing ethanol gradient (25%, 50%, 75% and 100%) for 5 minutes each at room temperature and air dried. Prepared samples were gently scraped onto aluminum stubs coated in carbon tape and viewed in a Zeiss Ultra Plus high-resolution scanning electron microscope (Carl Zeiss, Inc).

FA adsorption and degradation experiments. 1) FA degradation by the ICS was compared to free cells in solution and to immobilized non-degrading cells. For that purpose, 60 mg of PEI-MMT composite were suspended in saline in 50 mL centrifuge tubes to a final volume of 2 mL. 8 mL of *P. putida* NS15 or *P. fluorescens* cell suspension were added to the composite; 8 mL of *P. putida* NS15 were added to 2 mL saline to serve as free cell controls. The final cell concentrations were 1.44·10$^9$ cells·mL$^{-1}$ in the case of free or immobilized *P. putida* NS15, corresponding to 2.5·10$^{11}$ cells·g$^{-1}$, and 0.82·10$^{11}$ cells·g$^{-1}$ (0.48·10$^9$ cells·mL$^{-1}$) for *P. fluorescens*.

2) FA degradation by the ICS was compared to free cells in solution and to immobilized non-degrading cells. For that purpose, 60 mg of PEI-MMT composite were suspended in saline in 50 mL centrifuge tubes to a final volume of 2 mL. 8 mL of *P. putida* NS15 or *P. fluorescens* cell suspension were added to the composite; free cell controls were added 2 mL saline instead of composite suspension. The final cell concentration was 1.28·10$^9$ cells·mL$^{-1}$ in all tubes, corresponding to 2.2·10$^{11}$ cells·g$^{-1}$ for immobilized cells.

To avoid loss of function over time due to repeated sampling, the experiment included four replicates of each type, three for data collection and an additional replicate from which the sampled replicates were refilled to keep their volume and composition constant. All four replicates were agitated at 25° C. for 1.5 hours, with a gauze cover to ensure an unlimited supply of oxygen. Tubes were then dosed with 740 ppm FA and agitated, closed, at 30° C. FA concentration was measured periodically; once the concentration in immobilized *P. putida* NS15 samples reached a low and constant value, tubes were given two more hours to allow regeneration, then spiked with a fresh dose of FA to reach a similar concentration across all samples. Refill tubes were added FA in proportion to remaining volume. The experiment did not include any separation steps, in order to compare the behavior of free cells and the ICS with minimal external influence.

The ICS carrying *P. putida* NS15 ($2.2 \cdot 10^{11}$ cells·g$^{-1}$) was tested using synthetic FA (from Fordor) and real WW from urea-formaldehyde resin production. The ICS was prepared as described above (55 mL in total, in 250 mL flasks), centrifuged and gently suspended in saline to 10 mL. Fordor or WW were added to duplicates of the ICS to yield final concentrations of 5800 ppm FA.

Initial removal rates (ppm·h$^{-1}$ and mg·g$^{-1}$·h$^{-1}$) were calculated by normalizing the amount removed within the first 30 minutes of each cycle to the time and composite weight.

Example 1

Composite Characterization

Figure 2:
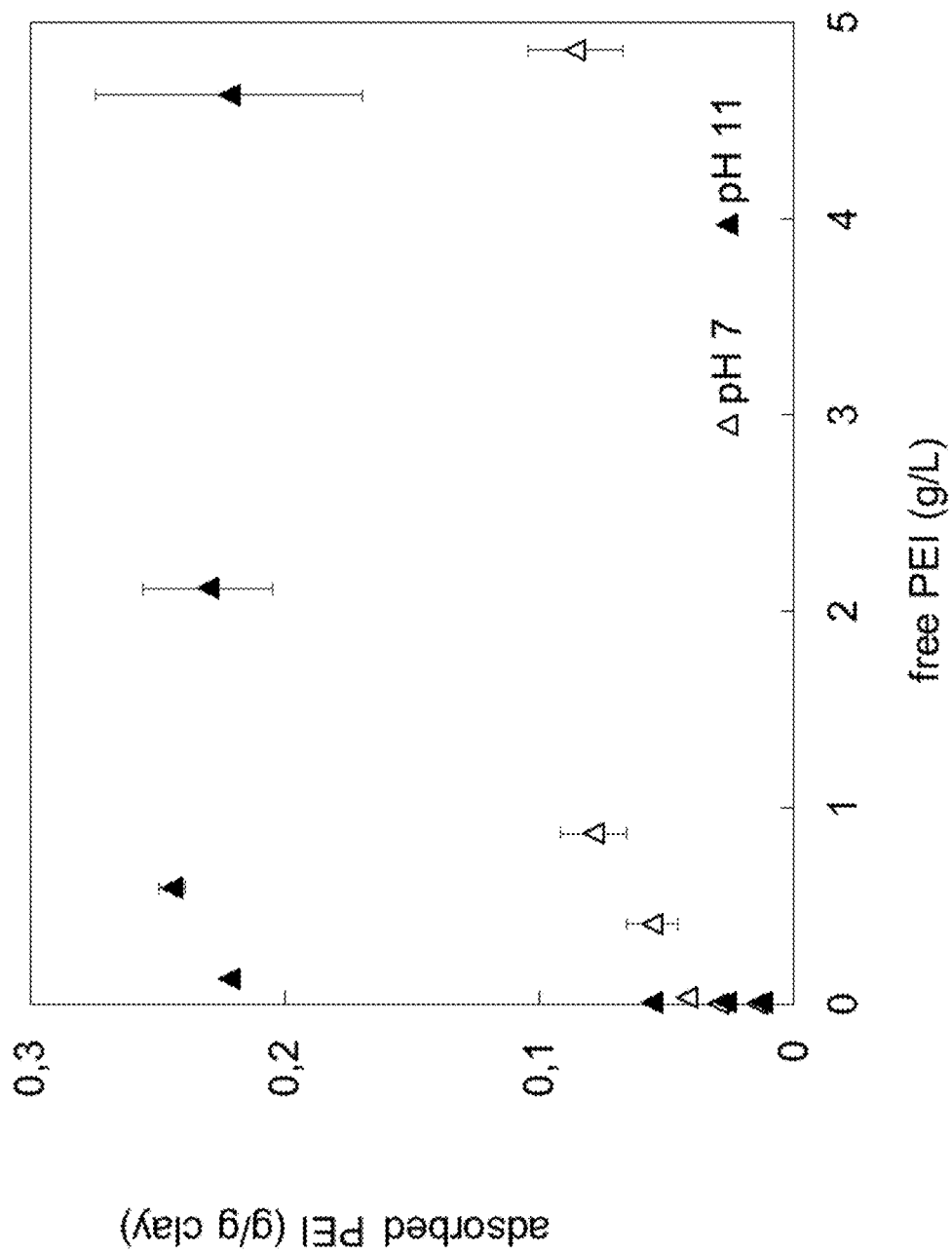
FIG. 2 presents the absorption isotherms of polyethylenimine (PEI) on montmorillonite clay (MMT) at different pH values.

The working hypothesis for the development of PEI-MMT composites was that in order to achieve high FA adsorption and bacterial immobilization—PEI loading on the clay needs to be maximized. In that respect, adsorption isotherms of PEI on MMT at pH 7 and 11 are presented in FIG. 2A, and characterization of selected PEI-clay composites (pH 7, 9 and 11) in Table 1. The results show PEI adsorption was limited at low pH and increased in an alkaline environment. This is probably due to the effect of pH on the charge density of MMT and PEI (pKa ~10.9). A further increase in the pH, from pH 11 to pH 11.5, resulted in a maximal loading of 300 mg per g clay. Zeta potential increased as a function of polymer loading on the clay and charge reversal was measured well below the CEC of the clay due to the perturbation of the amine groups in the solution (results not shown). Zeta potential values of the composites at maximal loading were all positive and equivalent to the zeta potential of the free polymer in solution (41-36 mV), indicating external surface coverage (Table 1). Basal spacing calculations indicated intercalation of only one polymer-chain between the layers, which suggests that the increase in loading as a result of alkaline conditions is mainly on the external surface of the clay particles. Due to the high loading, all further experiments were done using the composite with the maximal loading of 300 mg·g$^{-1}$ clay.

TABLE 1

PEI loading, zeta potential, and basal spacing of composites prepared using 1 g · L$^{-1}$ PEI and 1.67 g · L$^{-1}$ MMT at different pH values.

| pH | PEI (mg · g$^{-1}$ clay) | Zeta potential (mV) | basal spacing (Å) |
|---|---|---|---|
| 7 | 78.89 ± 13.07 | 41.20 ± 1.39 | 14.19 |
| 9 | 104.40 ± 8.29 | 41.80 ± 0.26 | 14.31 |
| 11 | 244.5 ± 5.12 | 36.03 ± 0.78 | 13.82 |

Example 2

Formaldehyde Adsorption

Figure 3C:
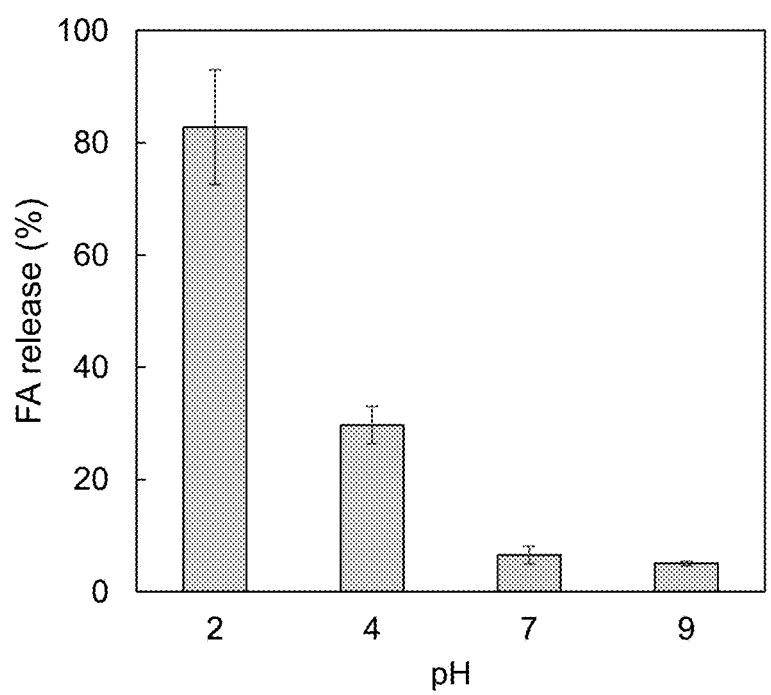

The mechanism governing FA adsorption to the composite is hypothesized to be via an aldehyde-amine condensation reaction that results in a covalently bonded imine group. The reaction is known to be reversible at pH<5. Indeed, FA adsorption experiments showed FA binding was strongly pH dependent, and was optimal around pH 9 (FIGS. 3A-C). Furthermore, the observed desorption was substantially higher at low pH values. The adsorption trend is in good agreement with the Langmuir model ($R^2=0.94$), with a calculated binding capacity of 62 mg FA·g$^{-1}$ composite and an adsorption coefficient kL=0.16 L·mg$^{-1}$. The model and pH dependency support the postulated binding mechanism, where covalent binding sites can be considered as finite and equally attractive chemisorption sites whose affinity towards FA is affected by the degree of amine protonation. The composite's performance in WW was also promising: FA adsorption from WW showed similar efficiency to adsorption from synthetic FA solutions (57 mg FA·g$^{-1}$ composite) and, at 30 g·L$^{-1}$ composite, the pH was naturally stabilized at 9, highly suitable for FA degradation by bacteria.

In terms of reaction kinetics, the quick removal of the main bulk of FA is crucial if the composite is to be used for cytotoxicity mediation. While equilibrium was not observed even after 48 hours, 80% of FA is adsorbed within 30 minutes, which is the more relevant time frame for application. FA binding to primary amines is hypothesized to be substantially more rapid than the reaction with secondary amines, which can explain the two stage kinetic behavior.

Figure 3D:
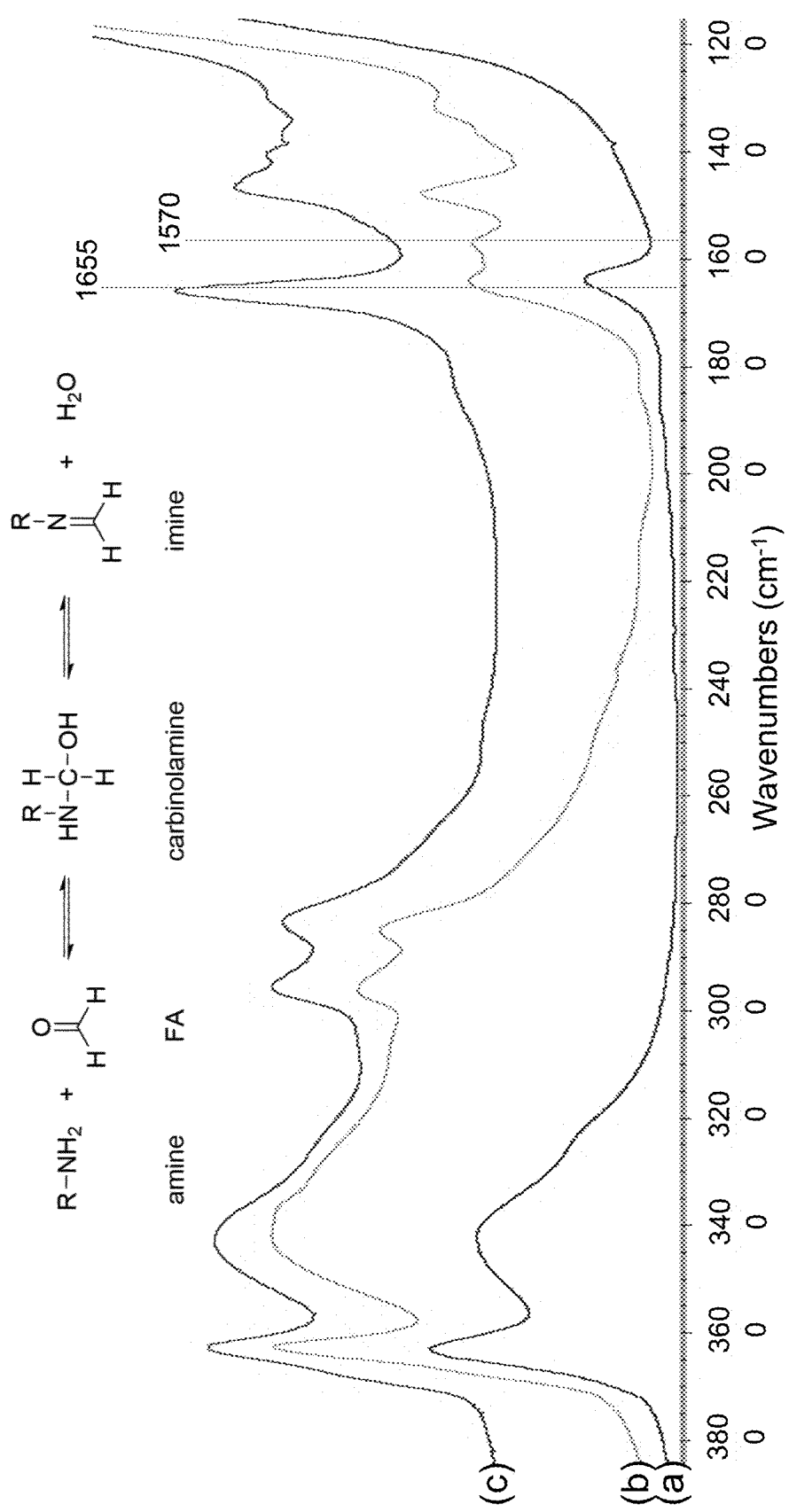

The IR spectra of MMT, the PEI-MMT composite, and a composite after FA adsorption are presented in FIG. 3D. Measurements revealed that FA binding to the composite was accompanied by a structural change: Both PEI and the carbinolamine intermediate formed during FA binding have $CH_2$ groups, which are represented by peaks around 1470 cm$^{-1}$ and 2800-3000 cm$^{-1}$ (the latter shift slightly after FA binding, which might suggest a change from 1° to 2° amines.) The primary amino groups of PEI have additional bands at 1500-1640 cm$^{-1}$ and 3300-3500 cm$^{-1}$. These contribute a small bend to the 3400 cm$^{-1}$ peak of the PEI-MMT composite (FIG. 3D. (b)). This bend disappears after FA adsorption, along with the band at 1570 cm$^{-1}$ associated with N—H bending of 1° amines, confirming that FA has covalently bonded with the primary amines of PEI. The appearance of a band at 1400 cm$^{-1}$ and the shifting of the next band from 1640 cm$^{-1}$ to 1655 cm$^{-1}$ indicate the presence of imines and carbinolamines (FIG. 3D. (c)).

Example 3

Formaldehyde Degrading Bacteria

Figure 4A:
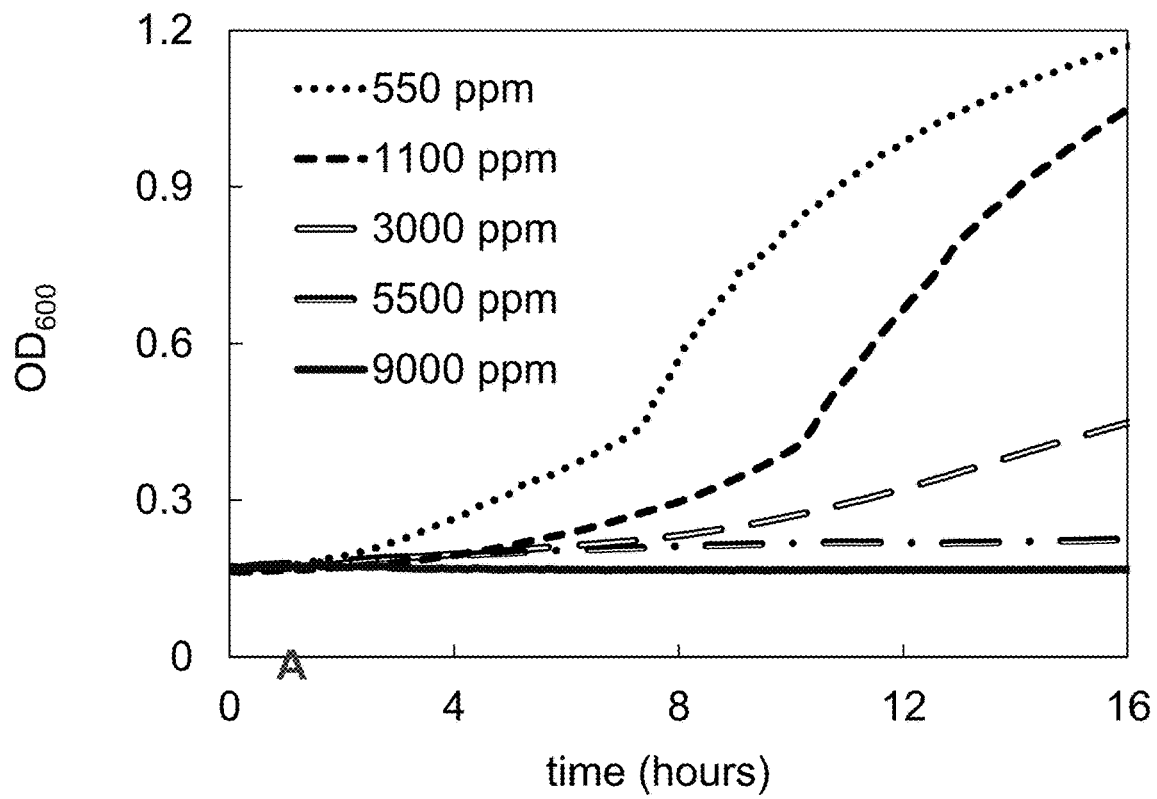
FIGS. 4A-B present graphs with Growth of *P. putida* NS15 at different FA concentrations (FIG. 4A) and Growth of *P. putida* NS15 at different pH levels (FIG. 4B)
Figure 4B:
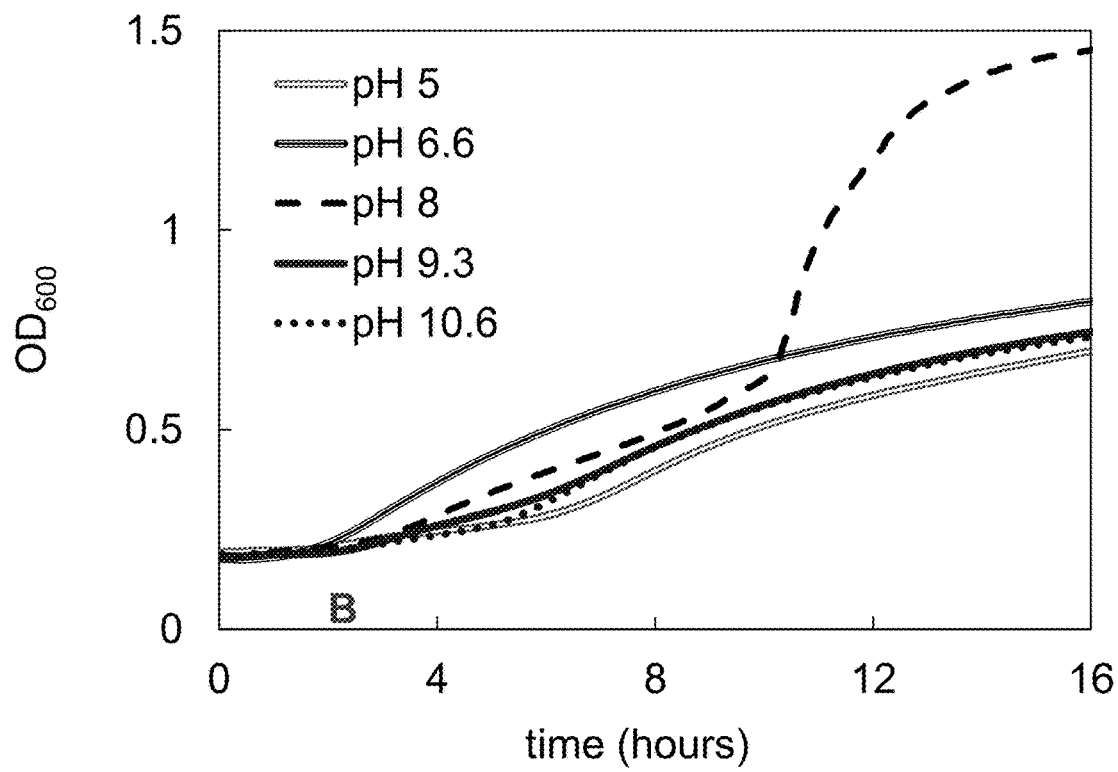

Over ten microbial strains capable of FA degradation were isolated from soil samples, largely identified as subspecies of the *Pseudomonas* genus. Isolates were able to degrade up to 97% of FA from a 370-ppm solution within four hours (FIGS. 4A-B). *P. putida* NS15 shows a strong preference to pH 8, and its growth was severely stunted at FA levels above 3000 ppm, reaffirming that the properties of FA in WW would be detrimental to bioremediation if free cell culture was used. When diluted to mild FA concentrations, the composition of WW proved to be no more toxic than synthetic FA formulations.

Example 4

Cell Immobilization

Figure 5A:
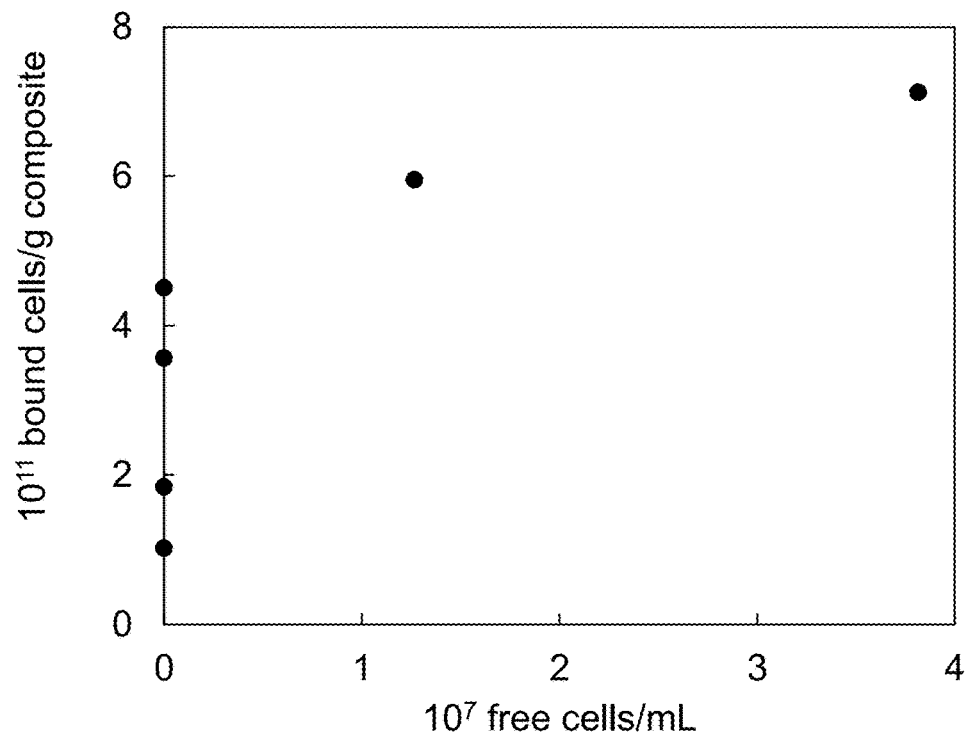
FIGS. 5A-C present graphs with adsorption isotherm of *P. putida* NS15 on the PEI-MMT composite (FIG. 5A) and zeta potential of ICS containing different amounts of *P. putida* NS15 cells (FIG. 5B) and SEM image of immobilized *P. putida* (2.5·10$^{11}$ cells/g composite) (FIG. 5C)
Figure 5B:
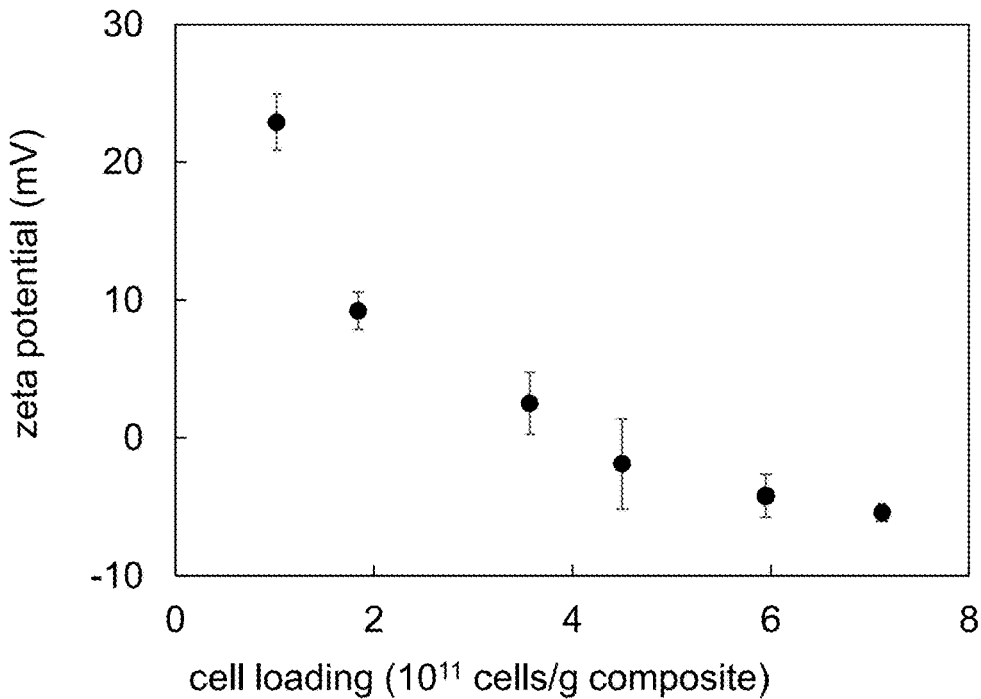
Figure 5C:
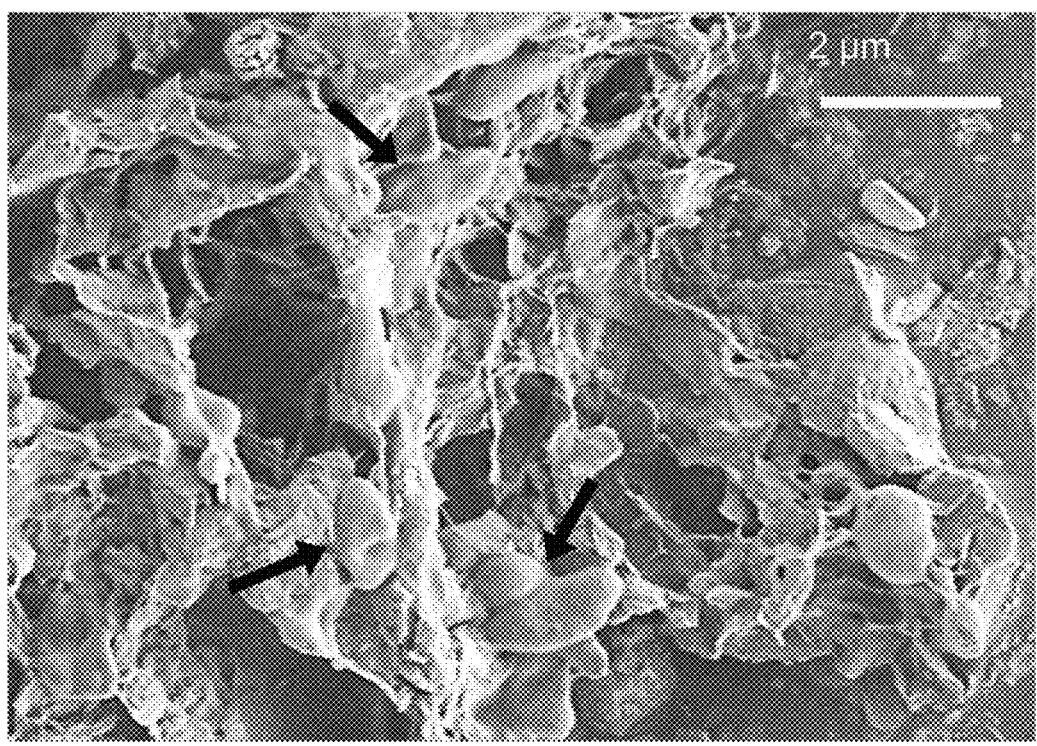

The Immobilized Cell System (ICS) was prepared by binding the bacteria to the PEI-MMT composite. Microbial adhesion to the composite was rapid, owing to electrostatic interactions between the positively charged surface and the negatively charged bacteria (FIG. 5A). As cell loading increased, the zeta potential of the resulting ICS decreased, becoming negative around the assumed binding capacity (FIG. 5B). The ICS was found to immobilize up to $4.5 \cdot 10^{11}$ cells·$g^{-1}$, however, an ICS carrying less bacteria than the maximal capacity was chosen for further testing in order to increase separation efficiency from free cells in solution. Electron micrographs of the chosen ICS showed bacterial attachment on and between the composite particles (FIG. 5C).

PEI has been reported to act as a permeabilizing agent, compromising the integrity of the bacterial cell wall without possessing inherent toxicity. Small lesions in the cytoplasmic membrane of immobilized *P. putida* NS15 could potentially exacerbate FA mineralization through improved metabolite transport, so long as environmental conditions are manageable. Therefore, the composites were tested for efficiency and compared in terms of activity and rate to free cell solutions.

Example 5

Simulations of Industrial Use

Figure 6A:
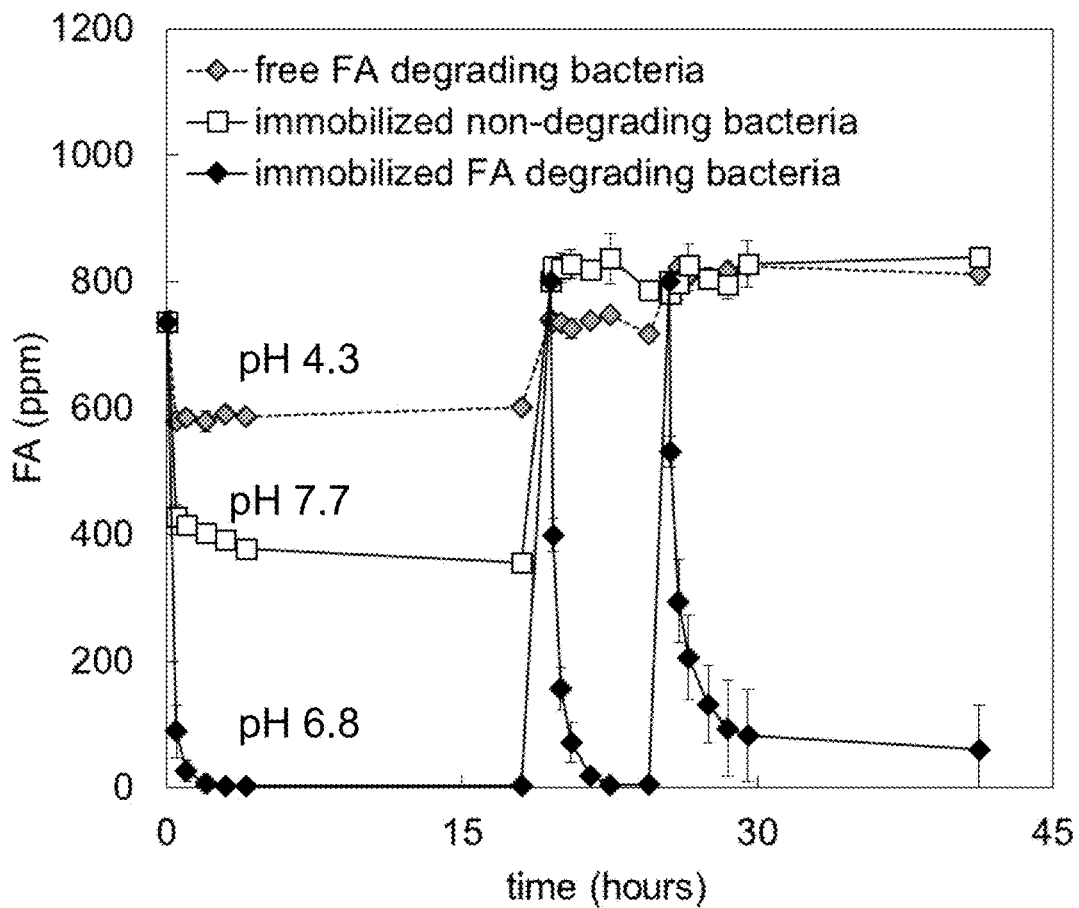
FIGS. 6A-B present graphs with FA removal by free or immobilized *P. putida* NS15 and inactive ICS carrying *P. fluorescens* (FIG. 6A) and FA release from used active (NS15) and inactive (P. fl.) ICS pellets (FIG. 6B)
Figure 6B:
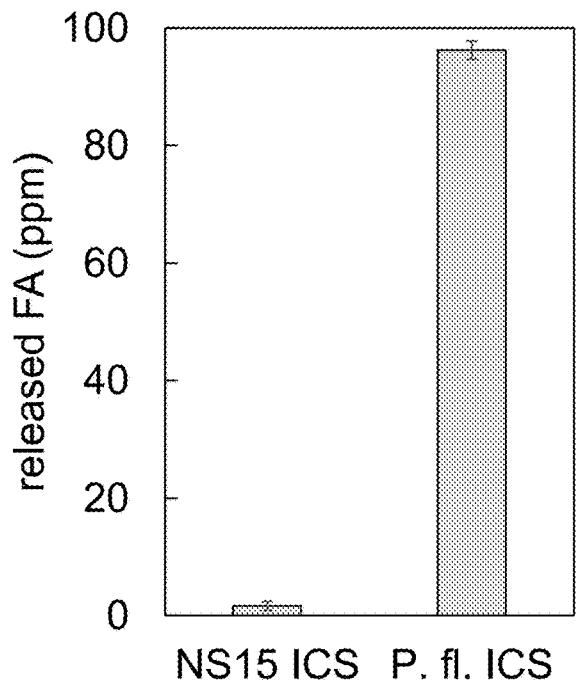

The FA remediation efficiency of the ICS was tested in comparison to free cells and immobilized non-degrading bacteria (*P. fluorescence*, inactive ICS), to highlight the contribution of FA adsorption to the functionality of the ICS (FIGS. 6A-B). The experiment was designed to give a fair comparison between the immobilized and suspended cells. Therefore, mechanically stressful procedures such as centrifugation and pellet resuspension were avoided.

The pH of the solution was monitored throughout the experiment. While free culture tubes encountered a considerably acidic pH, of 4.3, the pH in immobilized *P. putida* NS15 and immobilized *P. fluorescens* tubes was 6.8 and 7.7, respectively. The higher pH was a result of the PEI-MMT buffering capacity, which allows better biodegradation conditions for the active bacteria. In line with this observation, free cells could not degrade the FA efficiently and showed complete loss of activity after 1 hour. The inactive ICS became saturated with FA after 18 hours as well. For both the free cells and the inactive ICS, no adsorption or degradation was observed upon the second and third spiking of FA. On the other hand, immobilized *P. putida* NS15 cells retained their remediative traits and were able to remove over 15 times more FA than free cells before showing decline in activity.

FA release from the inactive and the active ICS after batch testing was performed by acid washing of the composites. Only a negligible amount of FA was released from the active ICS in comparison to the inactive ICS (~60-fold difference). This strongly suggests the bacteria managed to clean the composite and regenerate the material.

In terms of degradation rates, there was an apparent decrease from the first cycle to the third (6300-800 ppm FA·$h^{-1}$·$g^{-1}$), probably due to a decline in the buffering capacity of the ICS. Still, to the best of our knowledge, the initial rates either exceed or are equivalent to the rates in the reported literature, making this a promising solution.

In terms of industrial application, the ICS developed here has the potential to efficiently remove FA due to its three functionalities: Reducing FA in the waste-stream in order to reduce toxicity, buffering the waste-stream to an amicable pH for the bacteria, and the release of the bound FA to the co-localized cells in order to free binding sites for further FA binding and removal. Binding capacity was 62 mg FA·$g^{-1}$ composite and maximal dosage that can be applied is approximately 40 g·$L^{-1}$—this suggests that FA rich waste-streams in the order of 3000-5000 ppm can be effectively treated by the proposed material without any further dilution.

Example 6

Clay-Polymer Composite Characterization

The polymer-clay composite was designed to adsorb FA and immobilize FA degrading bacteria. Therefore, a branched PEI with a high primary and secondary amine content was chosen to modify the clay because: a) Clay and bacteria adhere to the protonated amine groups through electrostatic interactions, forming a stable composite. b) The amines react with FA to form aryl or alkyl carbon-nitrogen double bonds (Eq. 6). The latter is a well-known FA-amine reaction that is reversible and pH dependent, which allows control of the adsorption/desorption equilibrium $$R-NH_2 + CH_2O \rightleftharpoons R-NH=CH_2 + H_2O \qquad (6)$$

PEI adsorption to the clay is dependent on amine protonation and overall charge density. So, to achieve maximal loading of the polymer, adsorption was tested at several pH values; the resulting isotherms of PEI on MMT at pH 7.6 and 11 are presented in FIG. 7A, and characterization of selected PEI-clay composites (prepared at pH 7.6, 9, 11 and 11.5) in Table 2. The results show PEI adsorption was limited at low pH and increased in an alkaline environment. This is probably because high pH induces coiling of PEI (pKa ~10.9) and exposes more of the clay's surface area due to better dispersion of MMT. A further increase in the pH, from pH 11 to pH 11.5, yielded a maximal loading of approximately 300 mg per g clay. Consequently, all further experiments were done using the composite with this loading.

TABLE 2

PEI loading, zeta potential, and basal spacing of composites prepared using 1 g · $L^{-1}$ PEI and 1.67 g · $L^{-1}$ MMT at different pH values.

| pH | PEI (mg · $g^{-1}$ clay) | Zeta potential (mV) | basal spacing (Å) |
|---|---|---|---|
| 7.6 | 78.89 ± 13.07 | 41.20 ± 1.39 | 14.19 |
| 9 | 104.40 ± 8.29 | 41.80 ± 0.26 | 14.31 |
| 11 | 244.5 ± 5.12 | 36.03 ± 0.78 | 13.82 |
| 11.5a | 295.04 ± 5.34 | 36.67 ± 0.45 | 13.99 |

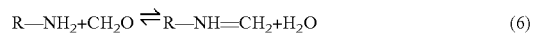
aPrepared using 3 g · $L^{-1}$ PEI and 5 g · $L^{-1}$ MMT.

Figure 8:
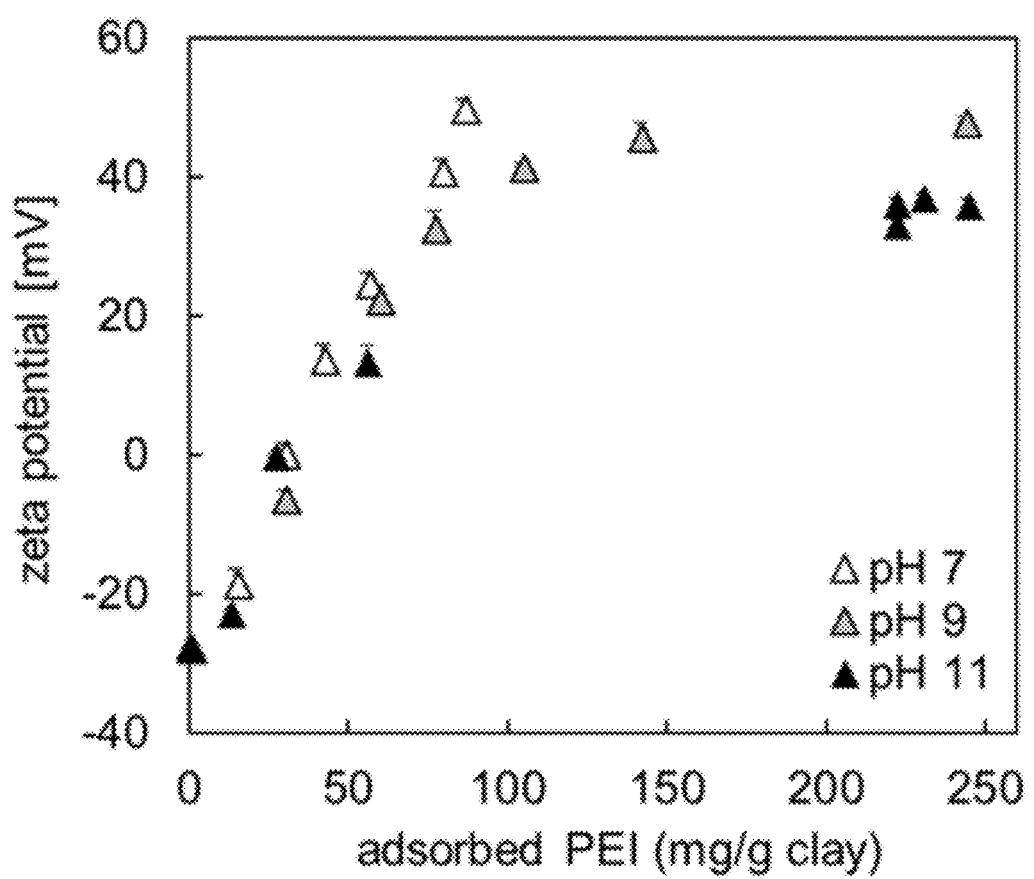
FIG. 8 presents a graph of the zeta potential of PEI-MMT composites prepared at pH 7.6, 9 and 11.
Figure 9A:
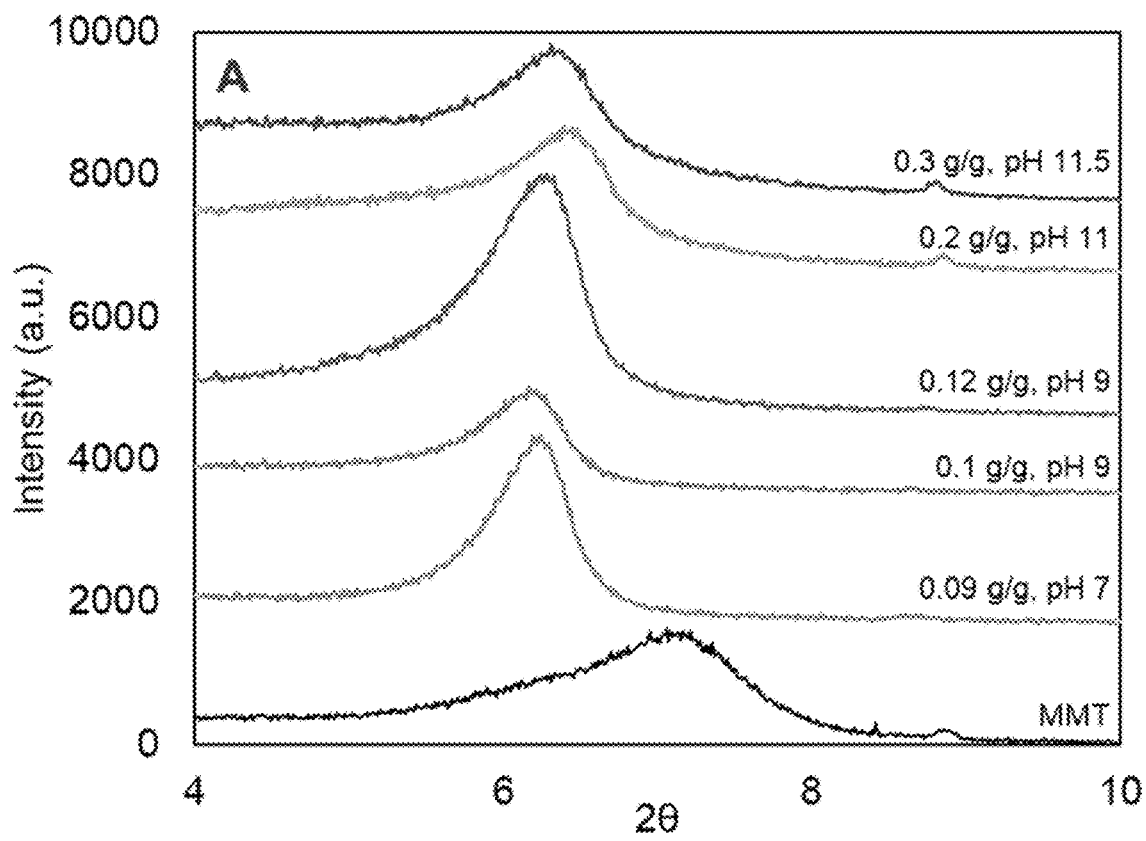
FIGS. 9A-B present X ray diffractograms of PEI-MMT composites before (FIG. 9A) and after (FIG. 9B) heating at 350° C.
Figure 9B:
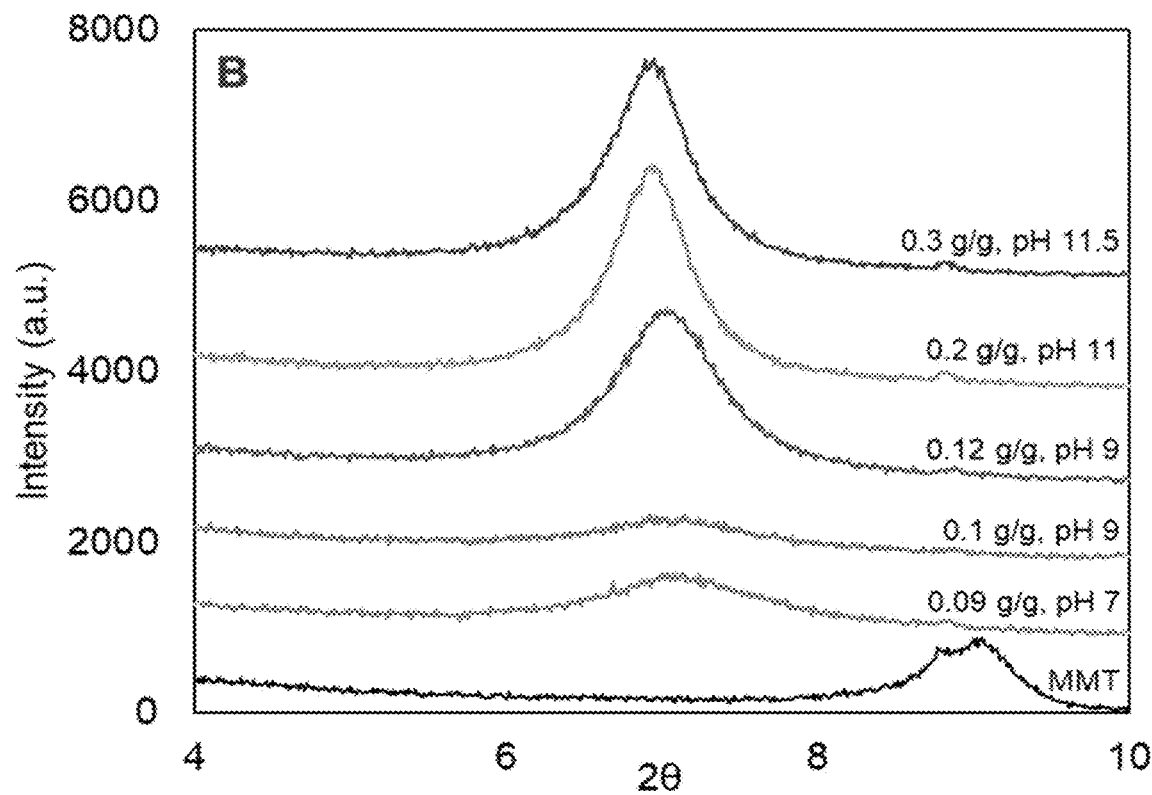
Figure 10:
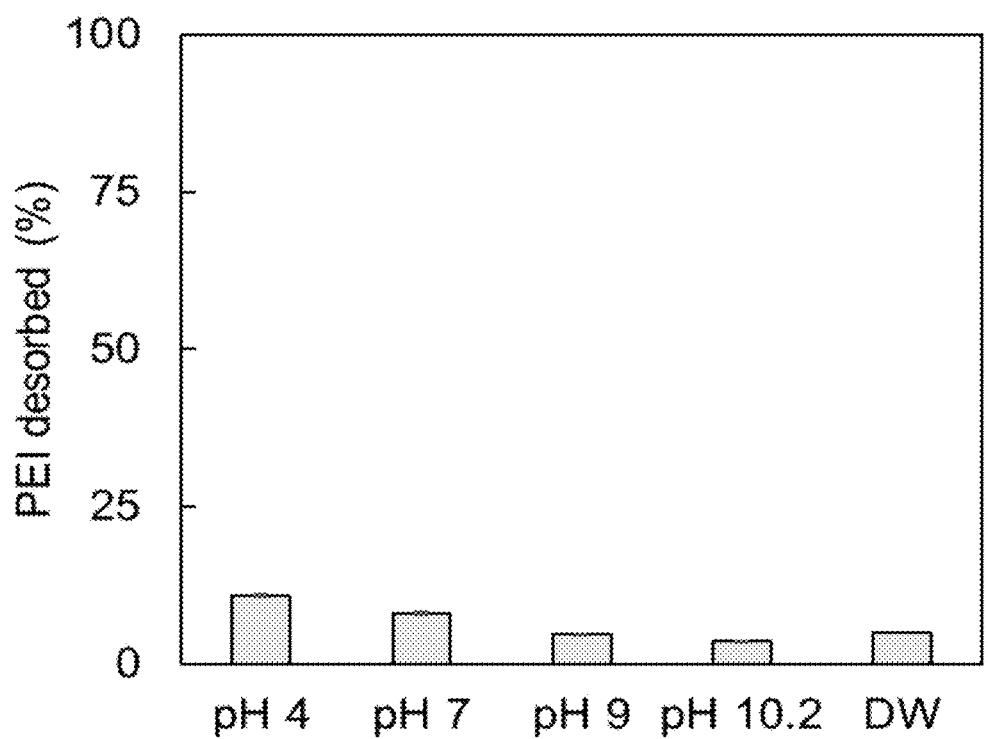
FIG. 10 presents a bar graph of PEI desorption (% from adsorbed) from the composite (300 mg·g$^{-1}$ clay) at different pH levels in saline and at ambient pH (10.2) in DW.

Zeta potential increased as a function of polymer loading on the clay, and charge reversal was measured well below the CEC of the clay due to amine groups protruding into the solution (FIG. 8). Zeta potential values of composites at maximal loading were all positive and equivalent to the zeta potential of the free polymer in solution (41-36 mV, Table 2). Basal spacing calculations indicated intercalation of only one polymer chain between the clay layers, which suggests that either surface coverage is incomplete at lower pH values or that additional adsorption at higher pH occurs mainly on exposed external surfaces (FIGS. 9A-B). Lastly, PEI desorption from the composites was found to be limited and not concerning in terms of application (FIG. 10).

Figure 11:
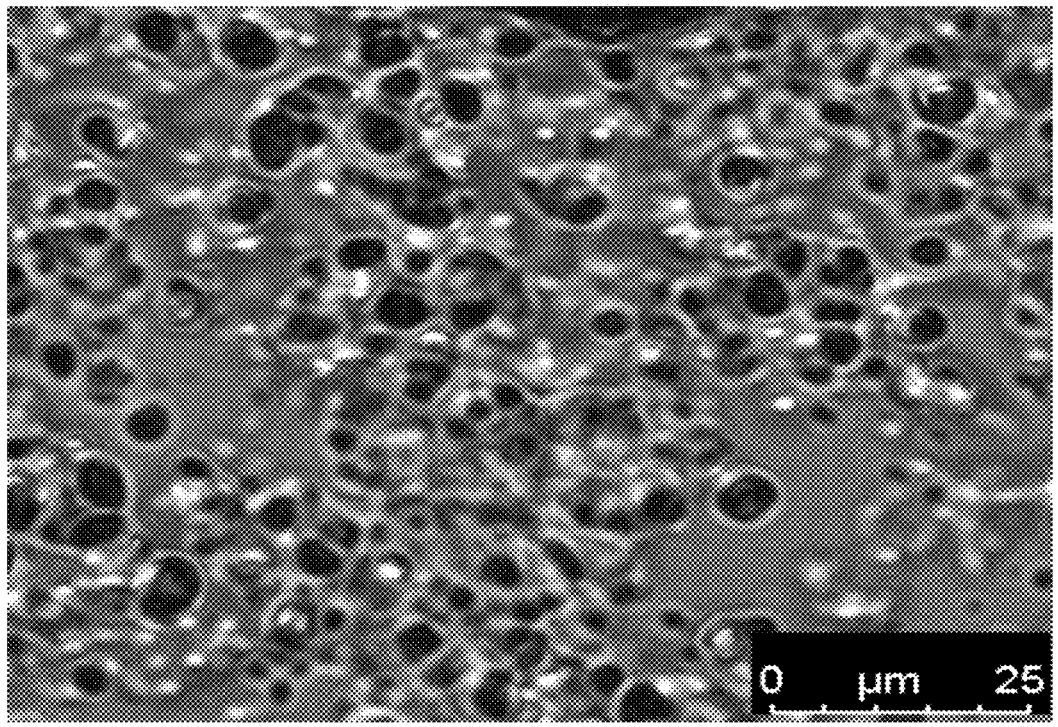
FIG. 11 presents Confocal micrograph of the PEI-MMT composite (300 mg·g$^{-1}$ clay)

DLS measurements of the native MMT and the PEI-MMT composite indicated an increase in particles size after modification with PEI, with the average diameter rising from 1.5 µm to 4 µm. This increase in the apparent diameter suggests that the composite forms small aggregates which were also observed under a confocal microscope (FIG. 11). These aggregates, unlike the native clay, are slightly larger than the average dimensions of the bacteria (1-2 µm in length and 0.5-0.7 µm wide), which allows bacteria to be immobilized on the surface of the composite aggregates.

The results from the zeta potential, DLS and XRD measurements confirm that the PEI-MMT composite could serve as an immobilization platform for bacteria, through electrostatic interactions between PEI and the microbial cells.

Example 7

Formaldehyde Adsorption

The amino groups of the PEI-MMT composites are hypothesized to adsorb FA via an aldehyde-amine condensation reaction, forming an imine group (see Eq 6). This structural change was identified in the IR spectra of MMT, the PEI-MMT composite, the composite after FA adsorption (FIGS. 3A-D).

The equilibrium of FA adsorption may shift back and forth, depending on environmental conditions such as pH.

Figure 12:
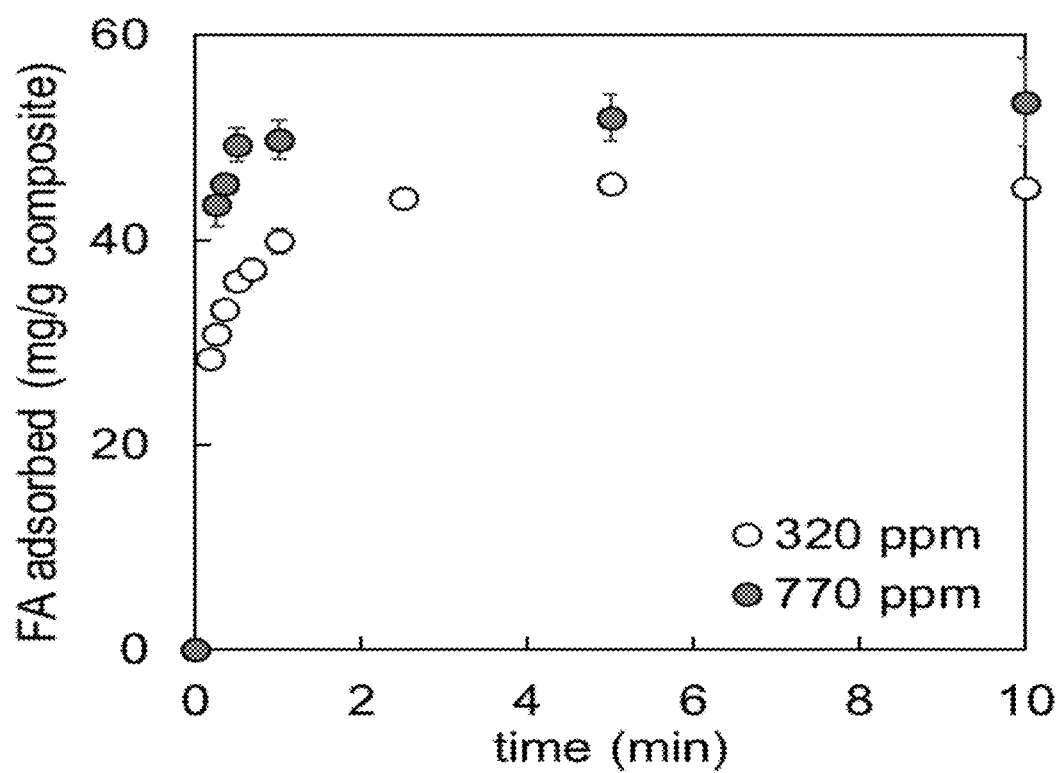
FIG. 12 presents adsorption kinetics of two concentrations of FA on PEI-MMT composite (300 mg·g$^{-1}$ clay)

The composite's capacity for FA (62 mg·g$^{-1}$) is among the highest reported in the literature for FA adsorption from water. Here, adsorption is intended to reduce FA levels so that biodegradation becomes possible. Fast adsorption is therefore just important as the adsorption capacity. The FA removal rate by the PEI-MMT composite is shown in FIG. 12. Approximately 90% of FA adsorption had occurred within one minute (FIG. 12 and Table 3).

TABLE 3

First and second order rate constants

| | | Pseudo-1$^{st}$ order | | | Pseudo-2$^{nd}$ order | | |
|---|---|---|---|---|---|---|---|
| FA (ppm) | $q_e$, meas. (mg·g$^{-1}$) | k (min$^{-1}$) | $q_e$, calc. | $R^2$ | K (mg·g$^{-1}$·min$^{-1}$) | $q_e$, calc. | $R^2$ |
| 320 | 45.18 | 5.445 | 41.59 | 0.959 | 0.1898 | 45.38 | 0.994 |
| 770 | 52.49 | 7.388 | 50.72 | 0.998 | 0.373 | 52.77 | 0.999 |

The composite's performance in WW was also promising: FA adsorption from WW (57 mg FA·g$^{-1}$ composite) was comparable to adsorption from synthetic FA solutions and, at 30 g·L$^{-1}$ composite, the pH was naturally stabilized at 9—supporting the hypothesis that the composite would be able to elevate the pH of FA solutions from approximately 4 to about 8, which is much more suitable for FA biodegradation.

Example 8

Formaldehyde Degrading Bacteria

Figure 13B:
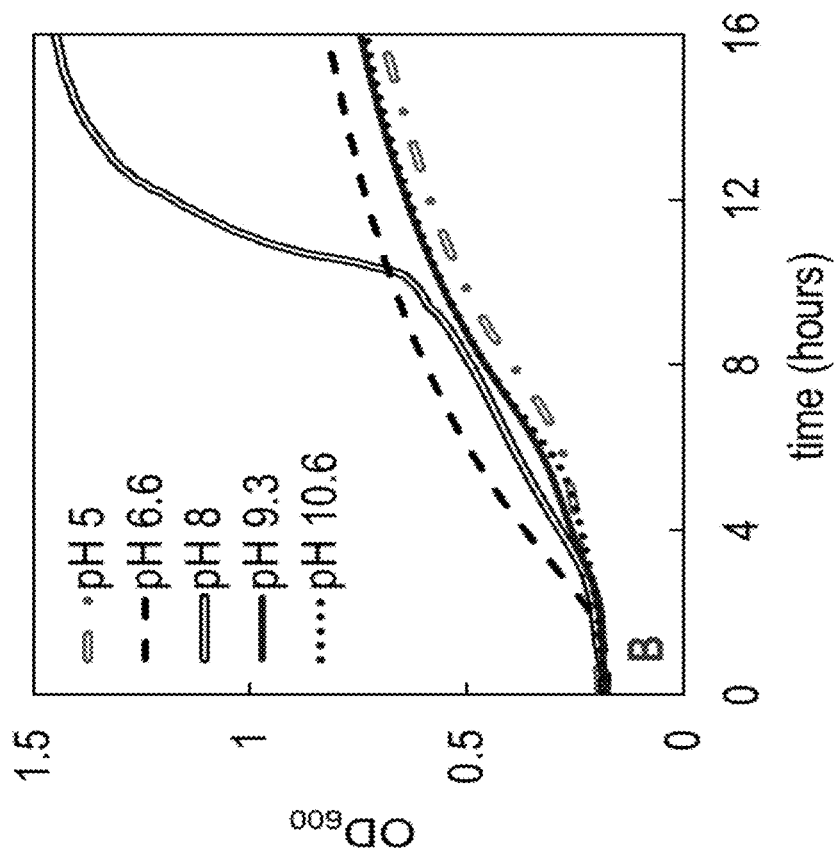
FIGS. 13A-B present graphs of growth of *P. putida* NS15 at different FA concentrations, pH 8 (FIG. 13A), and growth of *P. putida* NS15 at different pH levels with 925 ppm FA (FIG. 13B)
Figure 13A:
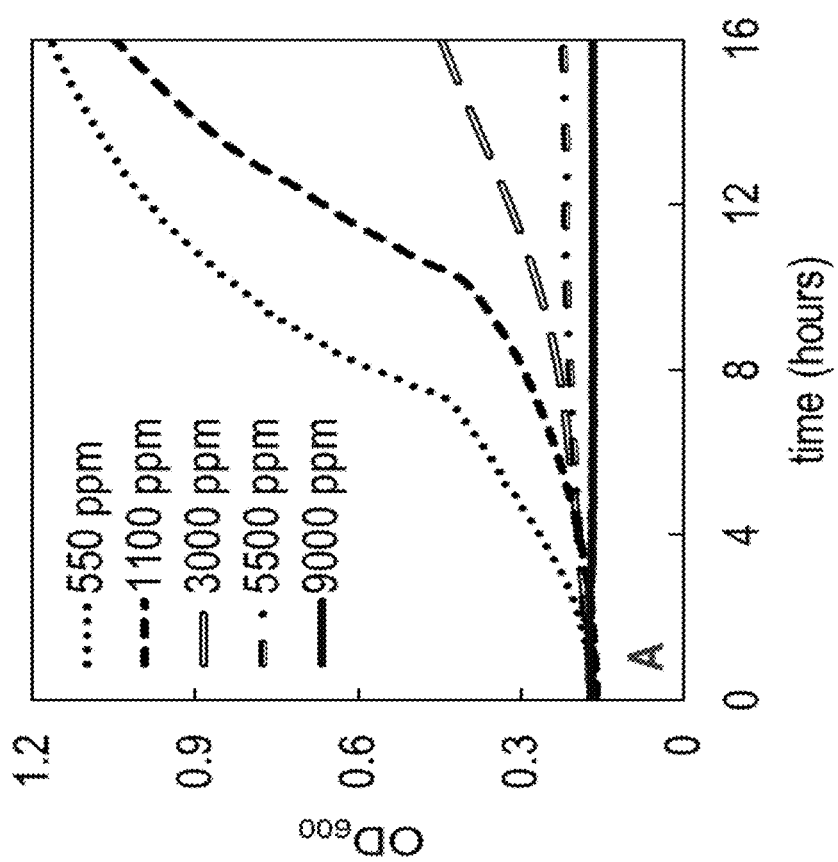

The last of the three components of the system are FA degrading bacteria. Soil derived *Pseudomonas putida* are known to degrade FA through two oxidation pathways that convert the toxic aldehyde to the safer formic acid, and then into $CO_2$. This metabolic transformation is part of a multifactorial response that makes *P. putida* particularly resistant to FA toxicity: besides direct biodegradation, it is able to extrude FA through a flux pump and express multiple enzymes to combat oxidative damage. The *P. putida* variant isolated in this study, marked NS15, was grown at several pH values and FA concentrations to estimate its tolerance to WW-like conditions (FIGS. 13A-B). *P. putida* NS15 shows a strong preference to pH 8, and its growth was severely stunted at FA levels above 3000 ppm, reaffirming that typical WW would be detrimental to bioremediation if a free cell culture was used. When diluted to mild FA concentrations, the composition of the obtained WW sample proved to be no more toxic than synthetic FA formulations.

Figure 14:
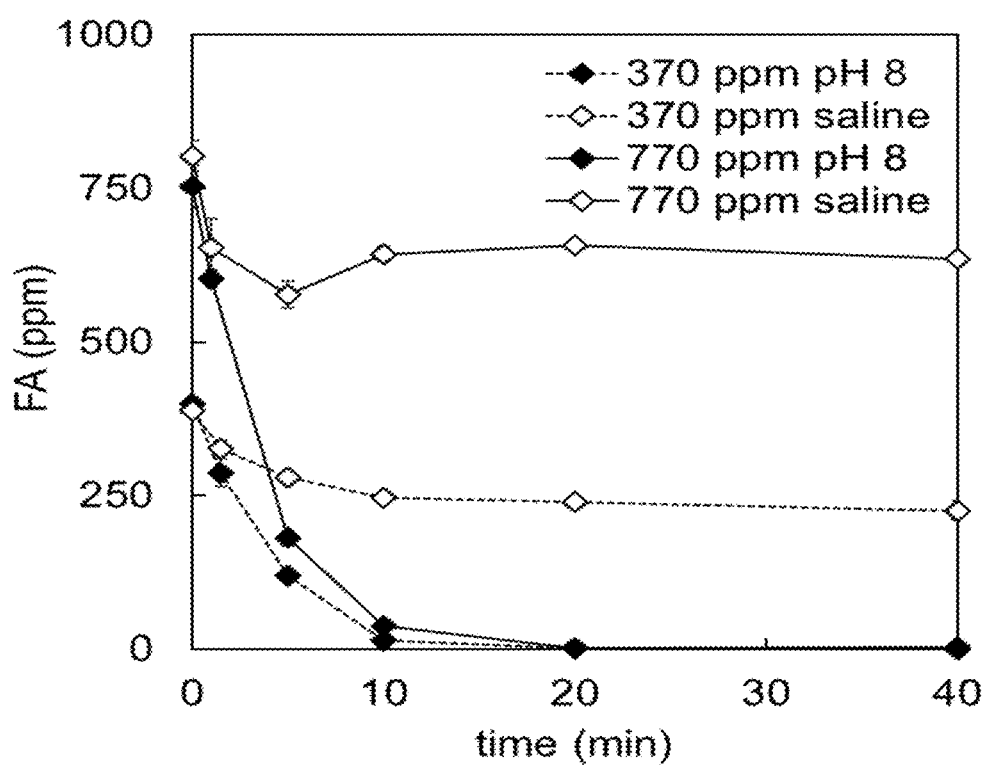
FIG. 14 presents degradation kinetics of two FA concentrations by *P. putida* NS15 in buffered and unbuffered solutions (1·10$^9$ cells·mL$^{-1}$)

FA biodegradation conforms to pseudo-first order kinetics, as seen in FIG. 14 and Table 4. The bacteria could degrade FA quickly in buffer, but failed to metabolize similar doses without pH adjustment. It should be noted that the adsorption rates of FA to the PEI-MMT composite were significantly faster (25 fold) than FA biodegradation rates; such quick removal by adsorption of the main bulk of FA is crucial if the composite is to be used for cytotoxicity mediation.

TABLE 4

First and second order rate constants at pH 8.

| | 1$^{st}$ order | | | 2$^{nd}$ order | |
|---|---|---|---|---|---|
| FA (ppm) | k (min$^{-1}$) | $R^2$ | | K (ppm.min$^{-1}$) | $R^2$ |
| 320 | 5.445 | 0.959 | | 0.1898 | 0.994 |
| 770 | 7.388 | 0.998 | | 0.373 | 0.999 |

Example 9

Cell Immobilization

Figure 15B:
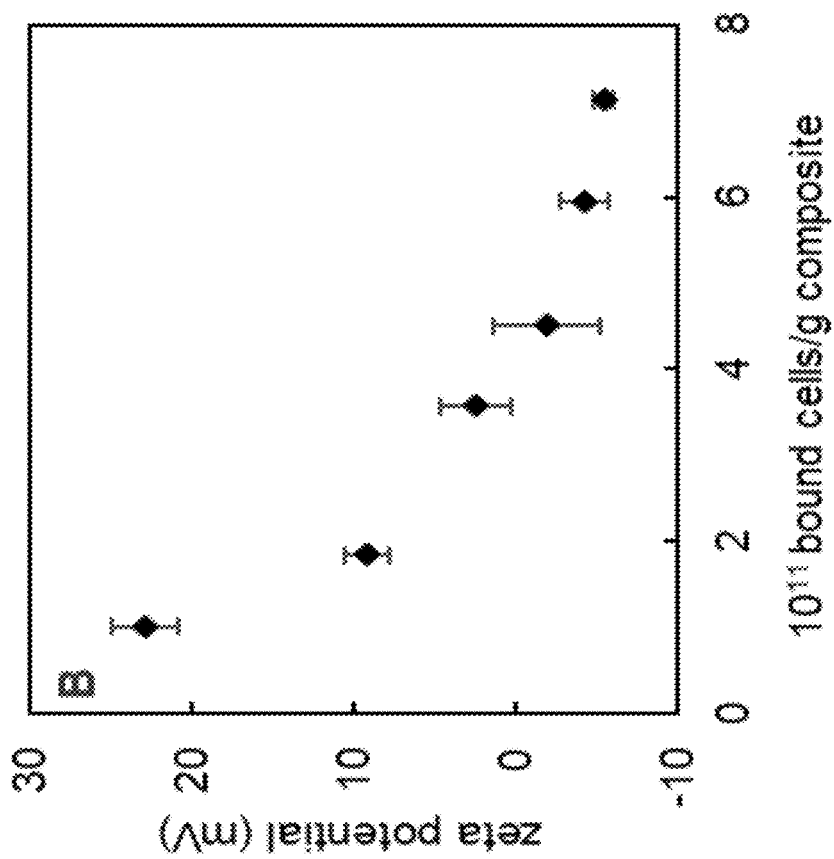
FIGS. 15A-C present adsorption isotherm of *P. putida* NS15 on the PEI-MMT composite (FIG. 15A), zeta potential of immobilized cell systems (ICS) containing different amounts of *P. putida* NS15 (FIG. 15B), and SEM image of immobilized *P. putida* NS15 (2.5·10$^{11}$ cells·g$^{-1}$); black arrows point to the bacteria (FIG. 15C)
Figure 15A:
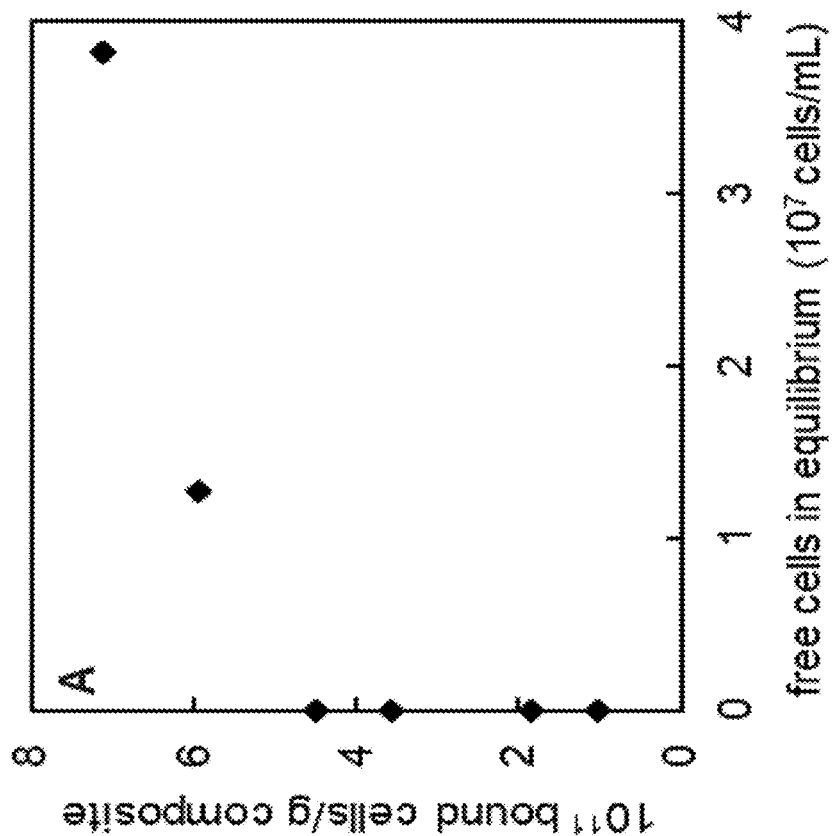
Figure 15C:
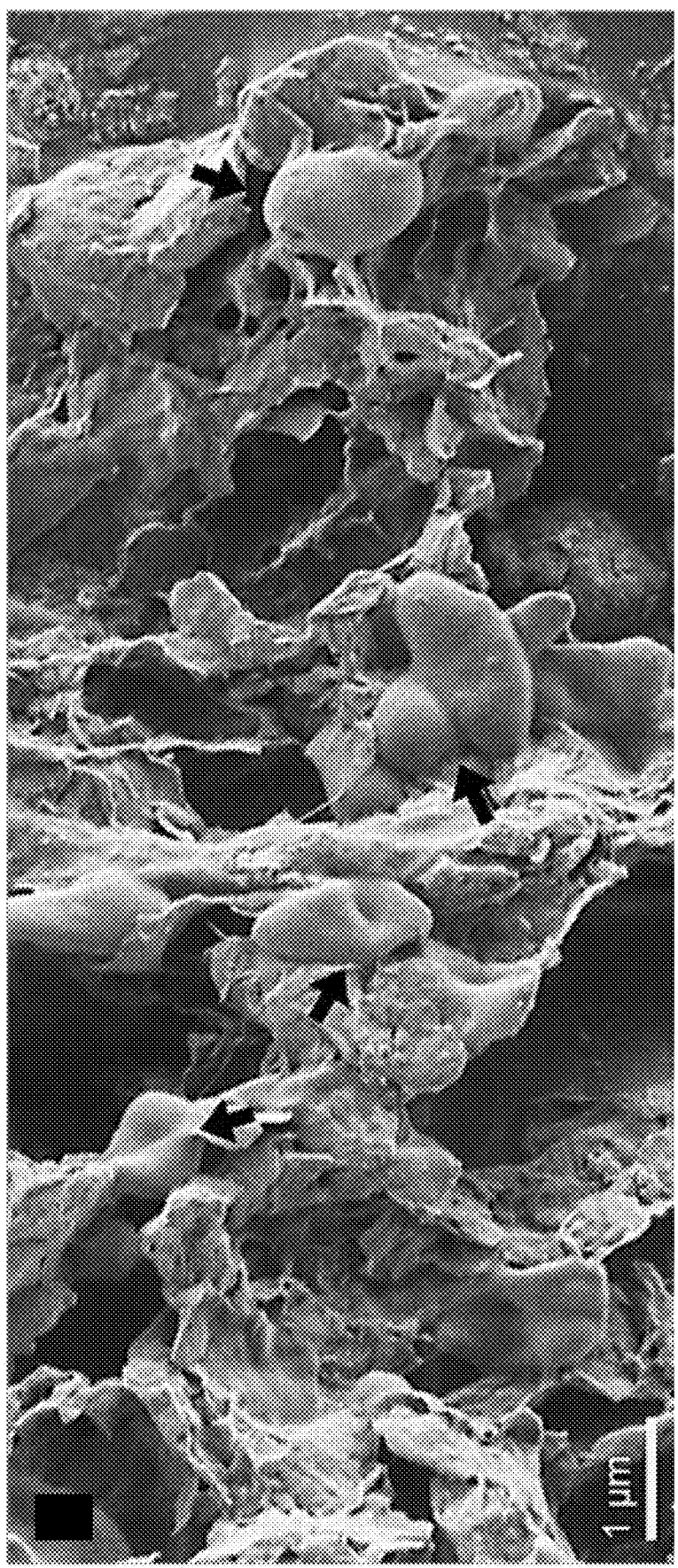

*P. putida* NS15 was bound to the PEI-MMT composite to produce an Immobilized Cell System (ICS). The affinity of the bacteria to the composite was high, owing to electrostatic interactions between the positively charged surface and the negatively charged bacteria (FIG. 15A). The bacteria and polymer-clay composite were mixed and left to settle, and the remaining unattached bacteria were measured to infer the bound fraction (bacteria alone did not settle in the allotted time). The zeta potential of the ICS decreased as the number of immobilized cells increased (FIG. 15B). The charge reversal was taken to represent the binding capacity—4.5·10$^{11}$ cells·g$^{-1}$. An ICS carrying fewer bacteria (only 2.5·10$^{11}$ cells·g$^{-1}$) was used in order to leave amine binding positions free for mediating pH and FA levels. At this loading, the bacteria are tightly bound by electrostatic forces and no unbound cells were detected. Electron micrographs of the ICS (2.5·10$^{11}$ cells·g$^{-1}$) showed bacterial attachment on and between the composite particles (FIG. 15C).

Example 10

Batch Degradation Tests

Figures 16A, 16B:
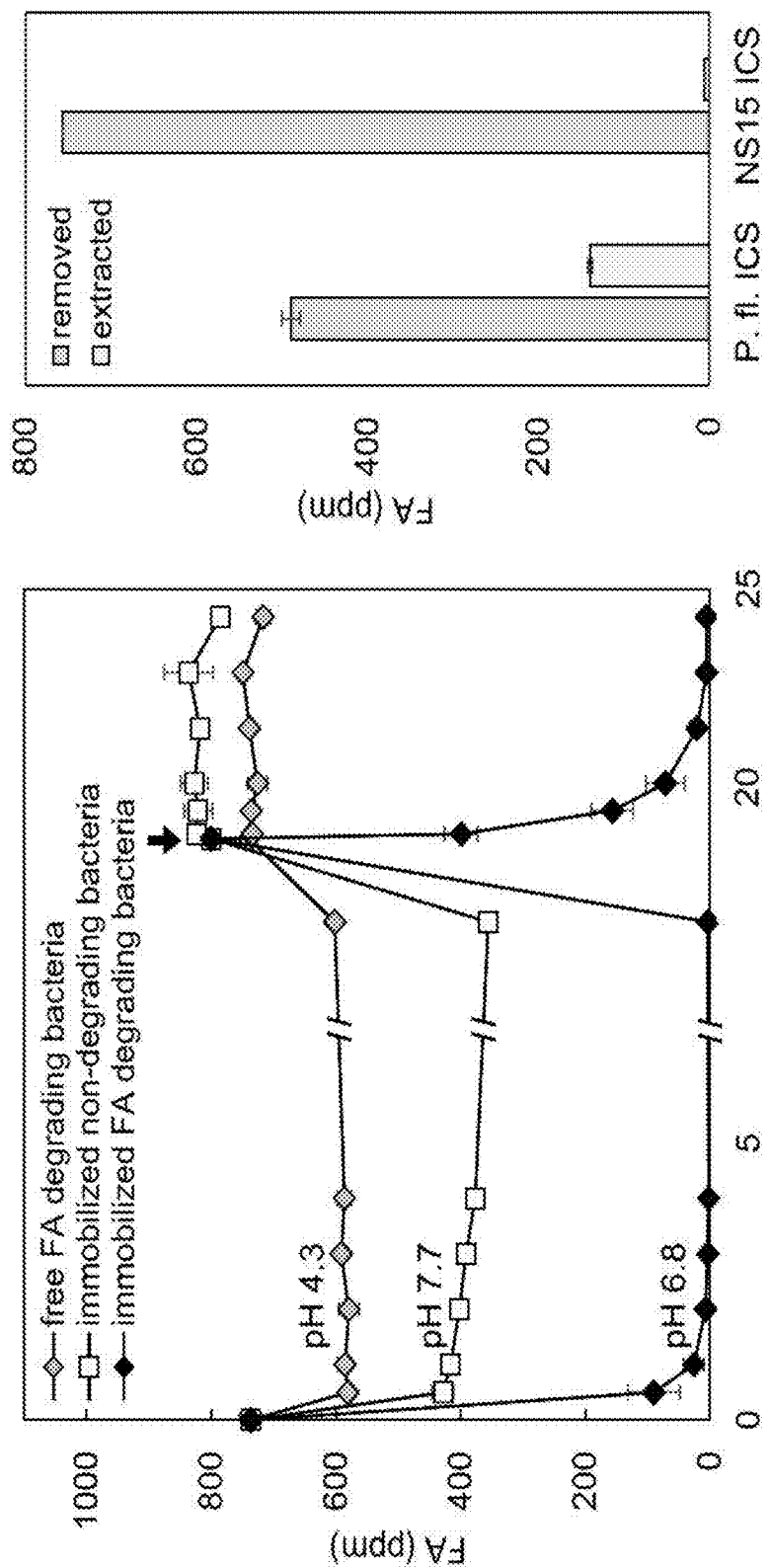
FIGS. 16A-C present graphs of two successive cycles of FA removal by free or immobilized *P. putida* NS15 and inactive ICS carrying *P. fluorescens* (1.28·10$^9$ cells·mL$^{-1}$, corresponding to 2.2·10$^{11}$ cells·g$^{-1}$ in the case of immobilized bacteria), arrow marks FA re-administration (FIG. 16A), FA removed (ppm) within a single cycle and FA that was acid-extracted from active (NS15) and inactive (P. fl.) ICS pellets post-treatment (FIG. 16B), and performance of the active ICS over 10 consecutive treatment cycles (FIG. 16C)
Figure 16C:
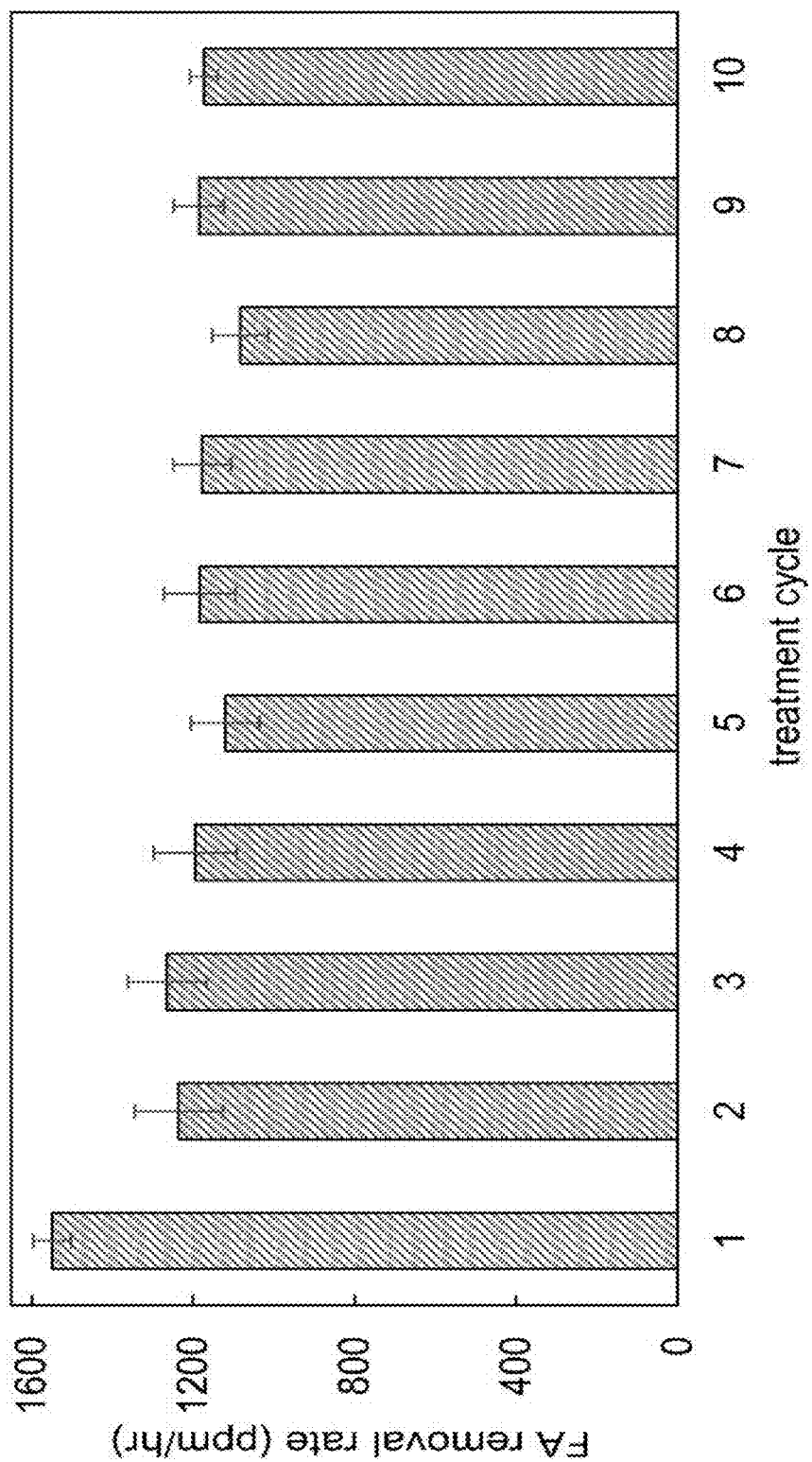

The FA remediation efficiency of the ICS was tested in comparison to free cells and immobilized non-degrading bacteria (*P. fluorescence*, inactive ICS) (FIGS. 16A-C). The experiment was designed to give a fair comparison between the immobilized and suspended cells. Therefore, mechanically stressful procedures such as centrifugation and pellet resuspension were avoided.

Both FA adsorption and biodegradation are expected to result in a pH drop, through the binding of primary amines and the production of formic acid. Therefore, the pH of the solution was monitored throughout the experiment. While the initial pH was circumneutral in all samples (Table 5), after FA addition the pH in free culture tubes decreased to 4.3.

TABLE 5

Experimental values of the batch removal experiment (synthetic FA solution).

| | Cell concentration ($10^9$ cells · $mL^{-1}$) | $FA_0$ (ppm) | FA @ 2 h (ppm) | $pH_0$ | pH @ 2 h |
|---|---|---|---|---|---|
| Free *P. putida* NS15 | 1.28 | 736.6 ± 18.2 | 579.3 ± 16.4 | 6.0 | 4.3 |
| Immobilized *P. putida* NS15 | 1.28 | 736.6 ± 18.2 | 7.0 ± 3.8 | 8.4 | 6.8 |
| Immobilized *P. fluorescens* | 1.28 | 736.6 ± 18.2 | 401.9 ± 10.6 | 8.3 | 7.7 |

No buffer other than the composite was added, which is why the initial pH values of the free and immobilized bacteria differ. The pH of the pristine PEI-MMT composite under similar conditions is 10.2.

The pH measured in immobilized *P. putida* NS15 and immobilized *P. fluorescens* tubes was 6.8 and 7.7 respectively (FIG. 16A). The higher pH recorded in immobilized cell samples can be attributed to the buffering capacity of the PEI-MMT composite. This capacity mitigates the decrease in pH and provides better biodegradation conditions for the active bacteria. In line with these observations, free cells could not degrade the FA efficiently and completely lost their activity after 1 hour. The inactive ICS became saturated with FA after 18 hours as well. For both the free cells and the inactive ICS, no adsorption or degradation were observed upon the second spiking of FA. In contrast, immobilized *P. putida* NS15 cells retained their remediative traits and were able to continuously remove FA from the solution.

Figure 17:
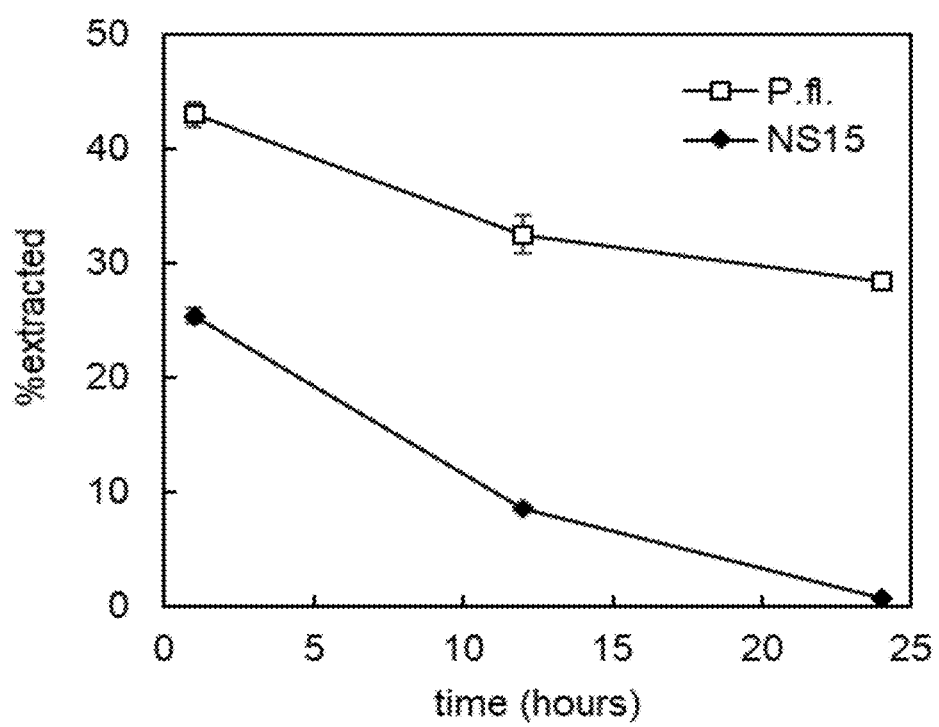
FIG. 17 presents a graph of acid-extraction of FA from the active (NS15) and inactive (P. fl.) ICS over the course of a single treatment cycle, as percent of the removed amount.

The regeneration of the composite's binding sites is instrumental in the successive use of the ICS. FA release from the active and inactive ICS after batch testing was performed by washing the composites at pH 2 (FIG. 16B). Only a negligible amount of FA was released from the active ICS in comparison to the inactive ICS. It should be noted that the recovery of FA extracted from the ICS was lower than from the composite without bacteria: 43% of adsorbed FA was recovered from the inactive ICS (FIG. 17), whereas over 80% FA was extracted from the composite without bacteria under the same conditions (FIG. 3C). This is perhaps because FA that enters the cells and binds to intracellular proteins is less prone to release. Nevertheless, the amount of FA extracted from the active ICS decreases from 23% to 0.78% over the course of the experiment (FIG. 17). This strongly suggests the bacteria degraded the fraction of FA slowly released from the surface and that FA-binding sites were regenerated.

Figure 18:
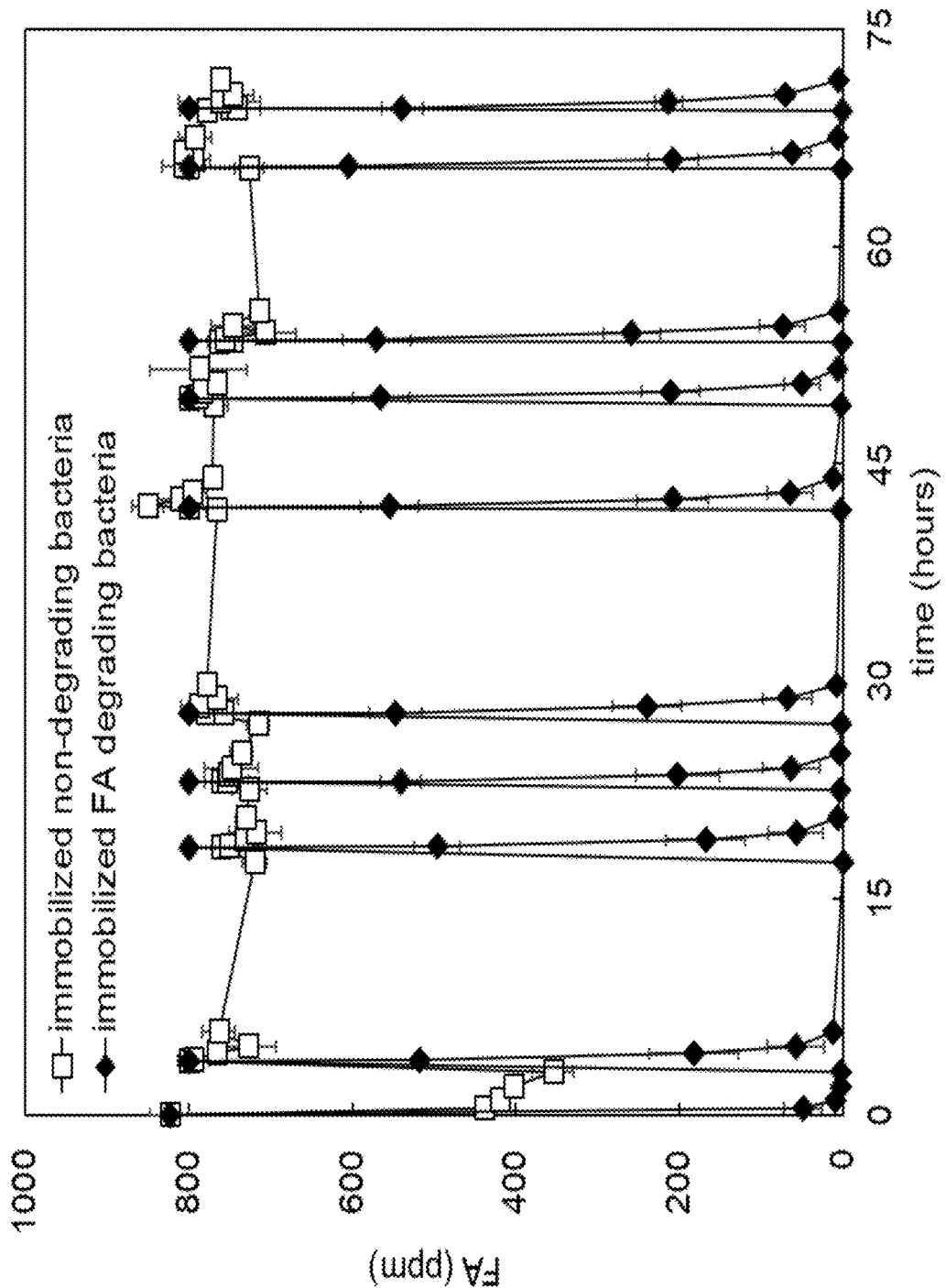
FIG. 18 presents a graph of performance of the ICS in ten successive treatment cycles (immobilized degrading bacteria, active ICS carrying *P. putida* NS15; immobilized non-degrading, inactive ICS carrying *P. fluorescens*); spikes in FA concentrations are the result of FA administration.

The ICS maintained high activity for 10 consecutive cycles, cumulatively removing more than 1400 mg·g composite$^{-1}$ (8000 ppm; FIG. 16C, FIG. 18). Additionally, initial removal rates were high, reaching 264-200 mg·g$^{-1}$·h$^{-1}$ (1600-1200 ppm·h$^{-1}$ at 5.7 g composite·L$^{-1}$), and the pH remained at a circumneutral level throughout the experiment.

Figure 19:
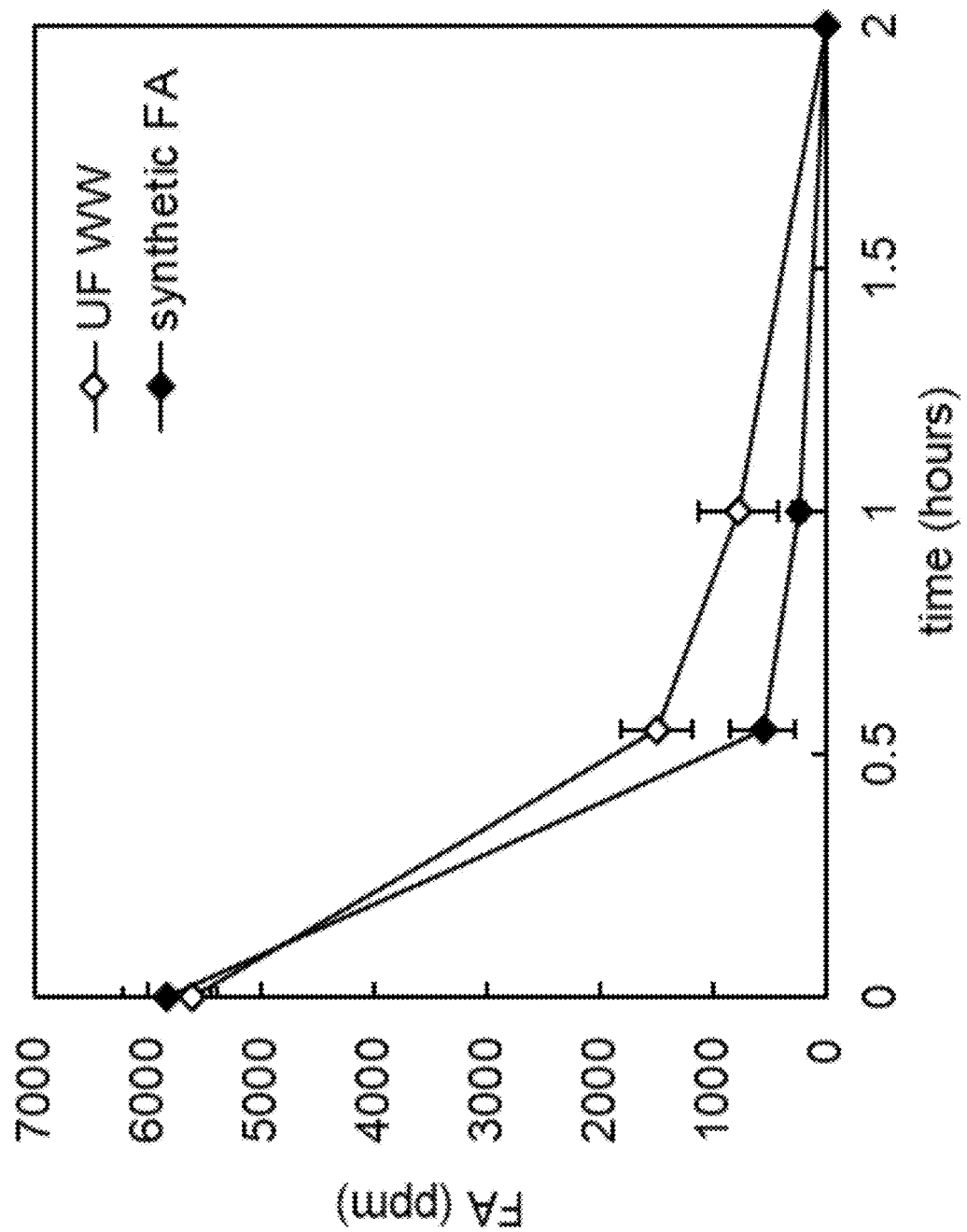
FIG. 19 presents a graph of FA removal from a synthetic solution and from real WW obtained from the production of urea-formaldehyde (UF) resin (32.5 g composite·L$^{-1}$, 2.2·10$^{11}$ cells·g$^{-1}$).

The binding capacity of the composite presented here was 62 mg FA·g$^{-1}$, and the maximal dosage that can be applied is approximately 40 g·L$^{-1}$. This suggests that FA rich WW in the order of 6000 ppm can be quickly and effectively treated by the proposed material without dilution or additional pH adjustment. Indeed, 5800 ppm FA was efficiently removed from both synthetic and real wastewater at the rate of 295 and 230 mg·g$^{-1}$·h$^{-1}$ respectively (FIG. 19).

For extremely concentrated waters, pH mediation is key, because bacteria are sensitive to the acidic conditions common in FA WW. Moreover, FA microbial degradation pathways usually involve the production of formic acid which also reduces pH. Combining adsorption (and subsequent slow release of FA) together with pH amendment and biodegradation, as demonstrated with this ICS, could help maintain appropriate pH levels.

The ICS developed here can efficiently remove FA due to its three unique features: 1. Reducing FA in the waste-stream in order to reduce toxicity, 2. buffering the waste-stream to an amicable pH for the bacteria, and 3. gradually releasing the bound FA to the co-localized cells, freeing binding sites for further treatment cycles. Our results show that the PEI-MMT composite was able to quickly reduce FA concentrations in solution, immobilize FA-degrading bacteria through electrostatic interactions, and sustain circumneutral pH levels for multiple bioremediation cycles.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition comprising:
   a. a mineral clay; and
   b. at least one polycation attached to at least a portion of a surface of the mineral clay; and
   c. at least one formaldehyde degrading microorganism;
   wherein said at least one polycation is a polyamine comprising primary amine groups, secondary amine groups or a combination thereof.

2. The composition of claim 1, wherein said polycation is attached to at least 25% of the total mineral clay surface; and wherein said polyamine is selected from poly-L-lysine, polyethylenimine (PEI), chitosan, and protamine.

3. The composition of claim 1, wherein said polycation has primary amine groups, secondary amine groups or a combination thereof.

4. The composition of claim 1, wherein said formaldehyde degrading microorganism is selected from *Methylobacterium, Paecilomyces, Pseudomonas, Aspergillus, Ralstonia*, methylotrophic yeast, *Pelobacter, Vibrio, Halomonas, Pseudoalteromonas, Bacillus, Escherichia coli, Saccharomyces cerevisiae, Zymomonas mobilis, Cupriavidus basilensis, Corynebacterium glutamicum, Candida*, or any combination thereof.

5. The composition of claim 1, wherein said microorganism is immobilized in said mineral clay surface up to $4.5 \cdot 10^{11}$ cells/g.

6. The composition of claim 1, having a zeta potential in the range of 1 to 100 mV.

7. The composition of claim 5, wherein said immobilized is an electrostatic interaction of the microorganism with an available amino group of the polycation.

8. The composition of claim 1, wherein said microorganism is present in a ratio ranging from $1 \cdot 10^{11}$ to $4.5 \cdot 10^{11}$ cells/g of polycation attached to the mineral clay surface.

9. The composition of claim 8, and wherein said at least one polycation comprises PEI, and wherein said mineral clay is selected from illite, phyllosilicate, Montmorillonite, sepiolite, attapulgite, hectoritebentonite, zeolite, aluminosilicate, smectite, and kaolinite.

10. The composition of claim 1, wherein said microorganism is viable in a solution containing up to 4000 ppm formaldehyde.

11. The composition of claim 1, wherein said at least one polycation is a branched PEI, and wherein said mineral clay is Montmorillonite.

12. The composition of claim 11, further comprising a solution of pH 3.5-4, or higher.

13. The composition of claim 1, wherein said composition for use in reducing formaldehyde concentration in a solution ranging from 5% to 100%.

14. The composition of claim 1, wherein said composition for use in reducing formaldehyde in a solution with a concentration of formaldehyde up to 8000 ppm.

15. The composition of claim 13, wherein said reducing formaldehyde is adsorbing, degrading or both.

16. A method for biodegradation of formaldehyde, comprising adding the composition of claim 1 to an formaldehyde containing environment, thereby reducing the formaldehyde concentration in said environment.

17. The method of claim 16, wherein said reducing formaldehyde is any one of (i) reducing formaldehyde concentration by at least 50-100%; (ii) adsorbing, degrading or both.

18. The method of claim 16, capable of reducing formaldehyde in a solution with a concentration of formaldehyde up to 8000 ppm.

19. The method of claim 16, wherein said adding the composition to an formaldehyde containing environment, is repeated up to 10 times.

* * * * *